(12) United States Patent
Blank et al.

(10) Patent No.: US 9,314,778 B2
(45) Date of Patent: Apr. 19, 2016

(54) CATALYSTS FOR HYDRODEOXYGENATION OF OXYGENATED HYDROCARBONS

(71) Applicant: Virent, Inc., Madison, WI (US)

(72) Inventors: Brian Blank, Monona, WI (US); Randy Cortright, Madison, WI (US); Taylor Beck, Madison, WI (US); Elizabeth Woods, Middleton, WI (US); Mike Jehring, Madison, WI (US)

(73) Assignee: Virent, Inc., Madison, WI (US)

( * ) Notice: Subject to any disclaimer, the term of this patent is extended or adjusted under 35 U.S.C. 154(b) by 0 days.

(21) Appl. No.: 14/585,852

(22) Filed: Dec. 30, 2014

(65) Prior Publication Data

US 2015/0141667 A1    May 21, 2015

Related U.S. Application Data

(63) Continuation of application No. 13/586,499, filed on Aug. 15, 2012, now Pat. No. 8,946,458.

(51) Int. Cl.
*C07D 315/00* (2006.01)
*B01J 27/195* (2006.01)
(Continued)

(52) U.S. Cl.
CPC ............. *B01J 27/195* (2013.01); *B01J 21/063* (2013.01); *B01J 21/066* (2013.01); *B01J 23/30* (2013.01);
(Continued)

(58) Field of Classification Search
CPC ...... B01J 27/195; B01J 21/063; B01J 21/066; B01J 23/30; B01J 23/42; B01J 23/44; B01J 23/626; B01J 23/6525; B01J 23/6527; B01J 23/888; B01J 23/8885; B01J 37/0201; B01J 27/04; C07C 49/00; C07D 307/08; C07D 309/02; C07D 309/04; C07D 309/06; C07D 407/04; C07D 307/33; C07D 307/36; C10G 3/42; C10G 3/50
USPC ......................................................... 549/415
See application file for complete search history.

(56) References Cited

U.S. PATENT DOCUMENTS 6,479,713 B1  11/2002  Werpy et al.
6,699,457 B2   3/2004  Cortright et al.
(Continued)

FOREIGN PATENT DOCUMENTS

EP    1232789 A1   8/2002
WO  2007075476 A2   7/2007
WO  2008109877 A1   9/2008

OTHER PUBLICATIONS

Dasari, et al., Low-Pressure Hydrogenolysis of Glycerol to Propylene Glycol, Applied Catalysis A: General, 2005, 281:225-231.
(Continued)

*Primary Examiner* — T. Victor Oh
(74) *Attorney, Agent, or Firm* — Quarles & Brady LLP

(57) ABSTRACT

The present invention provides catalysts, methods, and reactor systems for converting oxygenated hydrocarbons to oxygenated compounds. The invention includes methods for producing cyclic ethers, monooxygenates, dioxygenates, ketones, aldehydes, carboxylic acids, and alcohols from oxygenated hydrocarbons, such as carbohydrates, sugars, sugar alcohols, sugar degradation products, and the like, using catalysts containing palladium, molybdenum, tin, and tungsten. The oxygenated compounds produced are useful in the production of liquid fuels, chemicals, and other products.

20 Claims, 9 Drawing Sheets

(51) Int. Cl.
*B01J 23/42* (2006.01)
*B01J 23/44* (2006.01)
*B01J 23/652* (2006.01)
*B01J 23/888* (2006.01)
*B01J 37/02* (2006.01)
*C10G 3/00* (2006.01)
*C07C 27/04* (2006.01)
*B01J 21/06* (2006.01)
*B01J 23/30* (2006.01)
*B01J 23/62* (2006.01)
*C07C 49/00* (2006.01)
*C07D 307/08* (2006.01)
*C07D 307/33* (2006.01)
*C07D 307/36* (2006.01)
*C07D 309/02* (2006.01)
*C07D 309/04* (2006.01)
*C07D 309/06* (2006.01)
*C07D 407/04* (2006.01)
*B01J 37/08* (2006.01)

(52) U.S. Cl.
CPC  *B01J 23/42* (2013.01); *B01J 23/44* (2013.01); *B01J 23/626* (2013.01); *B01J 23/6525* (2013.01); *B01J 23/6527* (2013.01); *B01J 23/888* (2013.01); *B01J 23/8885* (2013.01); *B01J 37/0201* (2013.01); *C07C 27/04* (2013.01); *C07C 49/00* (2013.01); *C07D 307/08* (2013.01); *C07D 307/33* (2013.01); *C07D 307/36* (2013.01); *C07D 309/02* (2013.01); *C07D 309/04* (2013.01); *C07D 309/06* (2013.01); *C07D 407/04* (2013.01); *C10G 3/42* (2013.01); *C10G 3/50* (2013.01); *B01J 37/08* (2013.01); *C10G 2300/1014* (2013.01); *Y02P 30/20* (2015.11)

(56) References Cited

U.S. PATENT DOCUMENTS

| | | | |
|---|---|---|---|
| 6,953,873 | B2 | 10/2005 | Cortright et al. |
| 7,022,888 | B2 | 4/2006 | Choudhary et al. |
| 7,663,004 | B2 | 2/2010 | Suppes et al. |
| 7,767,867 | B2 | 8/2010 | Cortright |
| 7,977,517 | B2 | 7/2011 | Cortright et al. |
| 8,231,857 | B2 | 7/2012 | Cortright et al. |
| 8,933,281 | B2 | 1/2015 | Cortright et al. |
| 2010/0076233 | A1 | 3/2010 | Cortright et al. |
| 2011/0046419 | A1 | 2/2011 | Zhang et al. |
| 2012/0167876 | A1 | 7/2012 | Qiao et al. |
| 2012/0172588 | A1 | 7/2012 | Qiao et al. |
| 2012/0198760 | A1 | 8/2012 | Blommel et al. |

OTHER PUBLICATIONS

International Search Report and Written Opinion for PCT/US2013/055118 dated Nov. 19, 2013.

CATALYSTS FOR HYDRODEOXYGENATION OF OXYGENATED HYDROCARBONS

CROSS-REFERENCE TO RELATED APPLICATIONS

This application is a continuation of U.S. application Ser. No. 13/586,499 filed on Aug. 15, 2012, which is incorporated by reference herein.

TECHNICAL FIELD

The present invention is directed to catalysts and their use in the conversion of sugars, sugar alcohols, sugar degradation products (e.g., hydroxymethyl furfural (HMF), levulinic acid, formic acid, furfural, etc.), and other carbohydrates (e.g., polysaccharides, oligosaccharides, disaccharides, etc.) to lower molecular weight oxygenated compounds, such as polyols, alcohols, ketones, cyclic ethers, aldehydes, and carboxylic acids.

BACKGROUND OF THE INVENTION

Increasing cost of fossil fuel and environmental concerns have stimulated worldwide interest in developing alternatives to petroleum-based fuels, chemicals, and other products. Biomass (material derived from living or recently living biological materials) is one category of possible renewable alternative to such fuels and chemicals.

A key challenge for promoting and sustaining the use of biomass in the industrial sector is the need to develop efficient and environmentally benign technologies for converting biomass to useful products. A number of biomass conversion technologies unfortunately tend to carry additional costs which make it difficult to compete with products produced through the use of traditional resources, such as fossil fuels. Such costs often include capital expenditures on equipment and processing systems capable of sustaining extreme temperatures and high pressures, and the necessary operating costs of heating fuels and reaction products, such as fermentation organisms, enzymatic materials, catalysts, and other reaction chemicals.

One promising technology is the BioForming® platform being developed by Virent, Inc. The BioForming platform is based on the combination of aqueous phase reforming (APR) and/or hydrodeoxygenation (HDO) with conventional catalytic processing technologies, including acid condensation, base catalyzed condensation, acid catalyzed dehydration, and/or alkylation. In its operation, soluble carbohydrates extracted from biomass are introduced into a BioForming reactor with water as an aqueous feedstock. The aqueous carbohydrate feedstock is then converted into reactive intermediates through one or more APR/hydrodeoxygenation reactions. Once formed, the chemical intermediates undergo further catalytic processing to generate hydrocarbons for gasoline, jet fuel, diesel, or chemicals. Other aspects of the BioForming process are described in U.S. Pat. Nos. 6,699,457; 6,964,757; 6,964,758; and 7,618,612 (all to Cortright et al., and entitled "Low-Temperature Hydrogen Production from Oxygenated Hydrocarbons"); U.S. Pat. No. 6,953,873 (to Cortright et al., and entitled "Low-Temperature Hydrocarbon Production from Oxygenated Hydrocarbons"); U.S. Pat. Nos. 7,767,867; 7,989,664; and 8,198,486 (all to Cortright, and entitled "Methods and Systems for Generating Polyols"); U.S. Pat. Nos. 8,053,615; 8,017,818; and 7,977,517 and U.S. Patent Application Pub. Nos. 2011/0257448; 2011/0245543; 2011/0257416; and 2011/0245542 (all to Cortright and Blommel, and entitled "Synthesis of Liquid Fuels and Chemicals from Oxygenated Hydrocarbons"); U.S. Pat. No. 8,231,857 (to Cortright, and entitled "Catalysts and Methods for Reforming Oxygenated Compounds"); U.S. Patent Application Ser. No. 2010/0076233 (to Cortright et al., and entitled "Synthesis of Liquid Fuels from Biomass"); International Patent Application No. PCT/US2008/056330 (to Cortright and Blommel, and entitled "Synthesis of Liquid Fuels and Chemicals from Oxygenated Hydrocarbons"); and commonly owned co-pending International Patent Application No. PCT/US2006/048030 (to Cortright et al., and entitled "Catalyst and Methods for Reforming Oxygenated Compounds"), all of which are incorporated herein by reference.

One key step in the BioForming process is the ability to convert carbohydrates at moderate temperatures and pressures to produce intermediate compounds for further processing or use in industry. To be commercially effective, however, the process must be able to convert the carbohydrate feedstock to the necessary compounds at yields that are economical as compared to other technologies. The process must also effectively remove oxygen from the carbohydrate without a significant disruption of the corresponding carbon backbone.

Work has been done to allow the hydrogen generated during APR to be used in downstream processing of biomass and biomass-derived feedstocks to generate oxygenated hydrocarbons. Depending on current market conditions (such as the relative cost of biomass-derived feedstocks and other hydrogen sources), it can also be economically advantageous to supply external hydrogen. However, using external hydrogen can saturate the biomass feedstock such that it is completely deoxygenated into alkanes. Therefore, improved catalysts that are selective to avoid or minimize alkane generation while also maximizing mono- and polyoxygenate production in the presence of external hydrogen would be beneficial.

Researchers have recently developed methods to react pure hydrogen with sugars (xylose and glucose) and sugar alcohols (glycerol, xylitol, and sorbitol) over hydrogenation and hydrogenolysis catalytic materials to generate lower molecular weight compounds. For instance, U.S. Pat. Nos. 6,841,085; 6,677,385; and 6,479,713 to Werpy et al., disclose methods for the hydrogenolysis of both carbon-oxygen and carbon-carbon bonds in 5 and 6 carbon sugars using a rhenium (Re)-containing multimetallic catalyst to produce products, such as propylene glycol (PG). The Re-containing catalyst may also include Ni, Pd, Ru, Co, Ag, Au, Rh, Pt, Ir, Os and Cu. The conversion takes place at temperatures in a range from 140° C. to 250° C., and more preferably 170° C. to 220° C., and a hydrogen pressure between 600 psi to 1600 psi hydrogen.

Dasari et al. also disclose hydrogenolysis of glycerol to PG in the presence of hydrogen from an external source, at temperatures in a range from 150° C. to 260° C. and a hydrogen pressure of 200 psi, over Ni, Pd, Pt, Cu, and Cu-chromite catalysts. The authors reported increased yields of propylene glycol with decreasing water concentrations, and decreasing PG selectivity at temperatures above 200° C. and hydrogen pressures of 200 psi. The authors further reported that Ni, Ru, and Pd were not very effective for hydrogenating glycerol. Dasari, M. A.; Kiatsimkul, P.-P.; Sutterlin, W. R.; Suppes, G. J. *Low-pressure hydrogenolysis of glycerol to propylene glycol* Applied Catalysis, A: General, 281(1-2), p. 225 (2005).

U.S. Pat. No. 7,663,004 to Suppes et al., discloses a process for converting glycerin into lower alcohols having boiling points less than 200° C., at high yields. The process involves the conversion of natural glycerin to PG through an acetol intermediate at temperatures from 150° C. to 250° C., at a pressure ranging from 1 to 25 bar (14.5 to 363 psi), and preferably from 5 to 8 bar (72.5 to 116 psi), over a Pd, Ni, Rh, Zn, Cu, or Cr catalyst. The reaction occurs in the presence or absence of hydrogen, with the hydrogen provided by an external source. The glycerin is reacted in solution containing 50% or less by weight water, and preferably only 5% to 15% water by weight.

Regardless of the above, there remains a need for more cost-effective catalysts and methods for reacting complex and higher concentrations of carbohydrate feedstocks (e.g., polysaccharides, oligosaccharides, disaccharides, sugars, sugar alcohols, sugar degradation products, etc.), which are susceptible to thermal degradation at temperatures compatible with deoxygenation reactions, to the desired lower molecular weight oxygenated compounds, such alcohols, ketones, aldehydes, cyclic ethers, carboxylic acids and other polyols. To be cost effective, the catalysts employed must provide effective conversion to the desired compounds at higher yields and without significant saturation into alkanes.

SUMMARY OF THE INVENTION

The present invention is directed to catalysts and methods for converting oxygenated hydrocarbons to lower molecular weight oxygenated compounds using a heterogeneous catalyst containing palladium, molybdenum, tin, and tungsten on an acidic support. In one embodiment, the method includes reacting an aqueous feedstock solution with hydrogen, at a temperature between about 100° C. and about 300° C., in the presence of a heterogeneous hydrodeoxygenation (HDO) catalyst, to produce a reaction product comprising a cyclic ether and one or more oxygenated compounds selected from the group consisting of a polyol, a ketone, an aldehyde, a carboxylic acid, and an alcohol. The aqueous feedstock solution comprises water and one or more oxygenated hydrocarbons selected from the group consisting of a starch, a polysaccharide, an oligosaccharide, a trisaccharide, a disaccharide, a monosaccharide, a polyhydric alcohol, a sugar, a sugar alcohol, a sugar degradation product, and combinations thereof. The heterogeneous HDO catalyst comprises palladium, molybdenum, tin, and tungsten.

In one embodiment of the invention, the heterogeneous HDO catalyst contains at least 0.05 wt % palladium, at least 0.05 wt % molybdenum, at least 0.0125 wt % tin, and at least 0.1 wt % tungsten. In another embodiment, the heterogeneous HDO catalyst contains less than 5.0 wt % palladium, or less than 10.0 wt % molybdenum, or less than 5.0 wt % tin, or less than 20.0 wt % tungsten. In yet another embodiment, the heterogeneous HDO catalyst further comprises a support selected from the group consisting of nitride, carbon, silica, alumina, zirconia, titania, vanadia, ceria, boron nitride, heteropolyacid, kieselguhr, hydroxyapatite, zinc oxide, chromia, zeolites, tungstated zirconia, titania zirconia, sulfated zirconia, phosphated zirconia, acidic alumina, silica-alumina, sulfated alumina, iron aluminate, phosphated alumina, theta alumina, niobia, niobia phosphate, oxides of the foregoing, and mixtures thereof. The support may also be modified by treatment with a modifier selected from the group consisting of tungsten, titania, sulfate, phosphate, or silica.

The oxygenated hydrocarbons of the aqueous feedstock may comprise at least 5 wt % starches, or at least 5 wt % polysaccharides, or at least 5 wt % oligosaccharides, or at least 5 wt % trisaccharides, or at least 5 wt % disaccharides. In one embodiment, the aqueous feedstock further comprises lignin, lignin derivatives, ash components, or extractives. In another embodiment, the oxygenated compounds may further comprise a cyclic ketone.

The invention also includes a method of generating cyclic oxygenated compounds from oxygenated hydrocarbons by providing a feedstock comprising a solvent and at least one soluble oxygenated hydrocarbon, reacting the oxygenated hydrocarbon with hydrogen in the presence of the heterogeneous HDO catalyst at a reaction temperature and a reaction pressure to produce a reaction product comprising cyclic ethers and cyclic ketones. The heterogeneous HDO catalyst comprises palladium, molybdenum, tin, and tungsten. In one embodiment, the oxygenated hydrocarbon may have four or more carbon atoms. In another embodiment, the solvent may be selected from the group consisting of water, in-situ generated $C_{2+}$ $O_{2+}$ oxygenated hydrocarbons, recycled $C_{2+}$ $O_{2+}$ oxygenated hydrocarbons, bioreforming solvents, organic solvents, organic acids, and a mixture thereof.

In one embodiment the method of generating cyclic oxygenated compounds is carried out at a reaction temperature between about 100° C. and about 300° C., and a reaction pressure between about 70 psig and about 2000 psig. In another embodiment, the feedstock is contacted with the heterogeneous HDO catalyst at a weight hour space velocity (WHSV) of about 0.01 to about 10.0 grams of soluble oxygenated hydrocarbon per gram of heterogeneous HDO catalyst per hour.

The invention also provides a method for generating cyclic ethers. The method includes the steps of providing a heterogeneous catalyst comprising a support and a catalytic composition adhered to the support comprising palladium, molybdenum, tin, and tungsten; contacting the heterogeneous catalyst with hydrogen and an aqueous feedstock comprising a solvent and one or more oxygenated hydrocarbons selected from the group consisting of polysaccharides, oligosaccharides, trisaccharides, disaccharides, starches, sugars, sugar alcohols, sugar degradation products, and mixtures thereof, at (1) a temperature between about 100° C. to 300° C.; (2) a WHSV of greater than 0.01 gram of oxygenated hydrocarbon per gram of heterogeneous catalyst per hour; and (3) a pressure between about 70 psig to 2000 psig; producing a reaction product comprising cyclic ethers. In one embodiment, the reaction product is catalytically reacted with a condensation catalyst to produce $C_{4+}$ compounds selected from the group consisting of a $C_{4+}$ alcohol, a $C_{4+}$ ketone, a $C_{4+}$ alkane, a $C_{4+}$ alkene, a $C_{5+}$ cycloalkane, a $C_{5+}$ cycloalkene, an aryl, and a fused aryl. In another embodiment, the $C_{4+}$ compounds are distilled to provide a composition selected from the group consisting of an aromatic fraction, a gasoline fraction, a kerosene fraction, and a diesel fraction.

In one aspect of the invention, methods for regenerating the heterogeneous catalyst to reduce carbonaceous deposits on the catalyst are provided. In one embodiment, the method includes the steps of contacting the heterogeneous catalyst comprising palladium, molybdenum, tin, and tungsten with water and hydrogen in a reactor, at (i) a pressure between about 500 psig and about 2000 psig; (ii) a first temperature between about 150° C. and about 350° C.; purging the reactor with hydrogen; and increasing the temperature of the reactor from the first temperature to less than about 500° C. over a time period between about 1 hour and about 12 hours, to reduce carbonaceous deposits on the catalyst. In another embodiment, the method includes the steps of contacting the heterogeneous catalyst comprising palladium, molybdenum, tin, and tungsten with nitrogen in a reactor, at (i) a pressure between about 0 psig and about 100 psig; (ii) a first temperature between about 250° C. and about 375° C.; contacting the heterogeneous catalyst with a mixture comprising about 1% oxygen; and increasing the temperature of the reactor from the first temperature to less than about 500° C. over a time period between about 1 hour and about 16 hours, to reduce carbonaceous deposits on the catalyst.

In another aspect of the invention, a method for generating fuels and chemicals is provided. The method includes the steps of providing a feedstock comprising an oxygenated hydrocarbon and a solvent, the solvent comprising one or more members selected from the group consisting of water, in-situ generated $C_{2+}O_{2+}$ oxygenated hydrocarbons, recycled $C_{2+}O_{2+}$ oxygenated hydrocarbons, bioreforming solvents, organic solvents, organic acids, and a mixture thereof, and the soluble oxygenated hydrocarbon comprising polysaccharides, oligosaccharides, trisaccharides, disaccharides, starches, sugars, sugar alcohols, or sugar degradation products; catalytically reacting the oxygenated hydrocarbon with hydrogen over a heterogeneous catalyst comprising greater than 0.05 wt % palladium, greater than 0.05 wt % molybdenum, greater than 0.0125 wt % tin, and greater than 0.1 wt % tungsten, at a reaction temperature between about 100° C. and about 300° C., a reaction pressure between about 70 psig and about 2000 psig, and a WHSV of greater than 0.01 grams of soluble oxygenated hydrocarbon per gram of heterogeneous catalyst per hour, to produce a product mixture of oxygenated compounds comprising a cyclic ether, a polyol, a ketone, an aldehyde, a carboxylic acid, and an alcohol; catalytically reacting a portion of the product mixture in the presence of a condensation catalyst to produce $C_{4+}$ compounds; and distilling the $C_{4+}$ compounds to provide a composition selected from the group consisting of an aromatic fraction, a $C_4$-$C_9$ fraction, a $C_7$-$C_{14}$ fraction, and a $C_{12}$-$C_{24}$ fraction.

DESCRIPTION OF THE DRAWINGS

FIG. 1A is an exemplary HDO flow diagram. FIG. 1B is an exemplary HDO flow diagram with a recycle stream.

DETAILED DESCRIPTION OF THE INVENTION

Figure 1A:
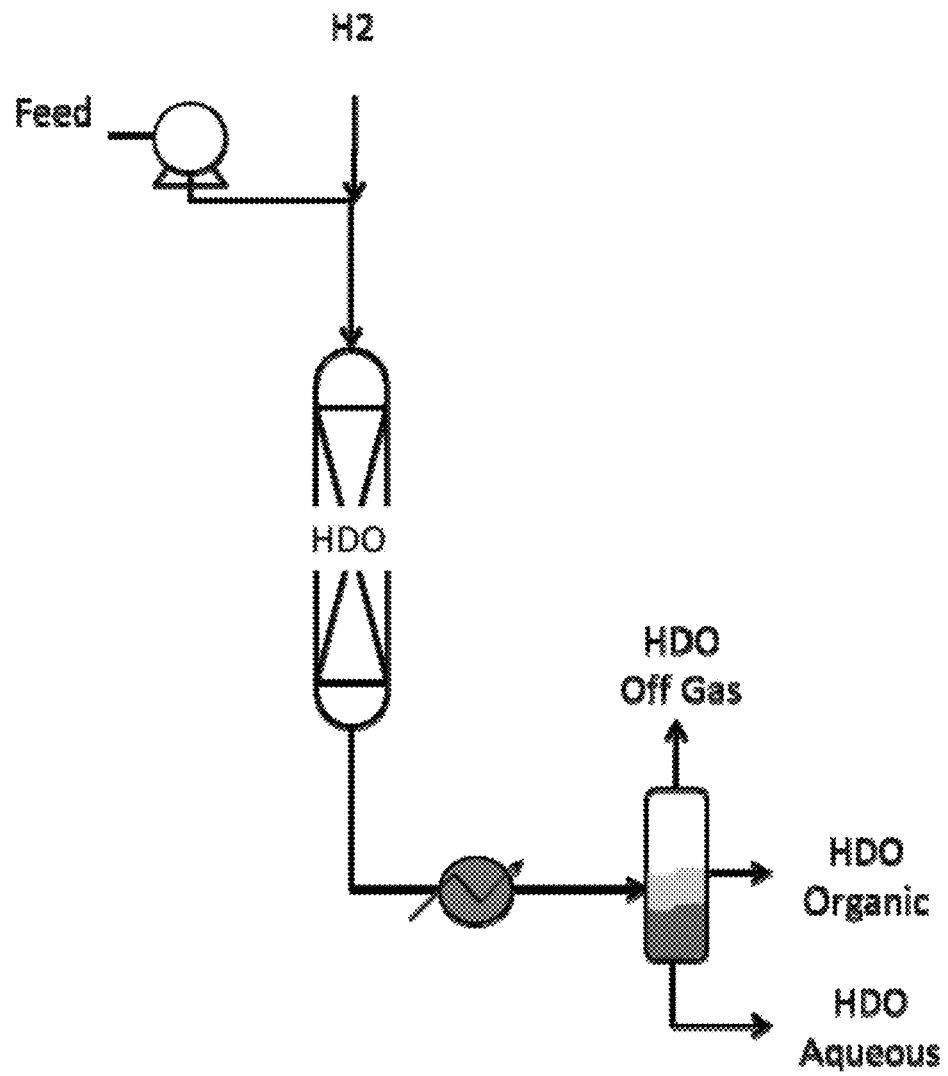
FIGS. 1A and 1B are flow diagrams illustrating two embodiments of the present invention.
Figure 1B:
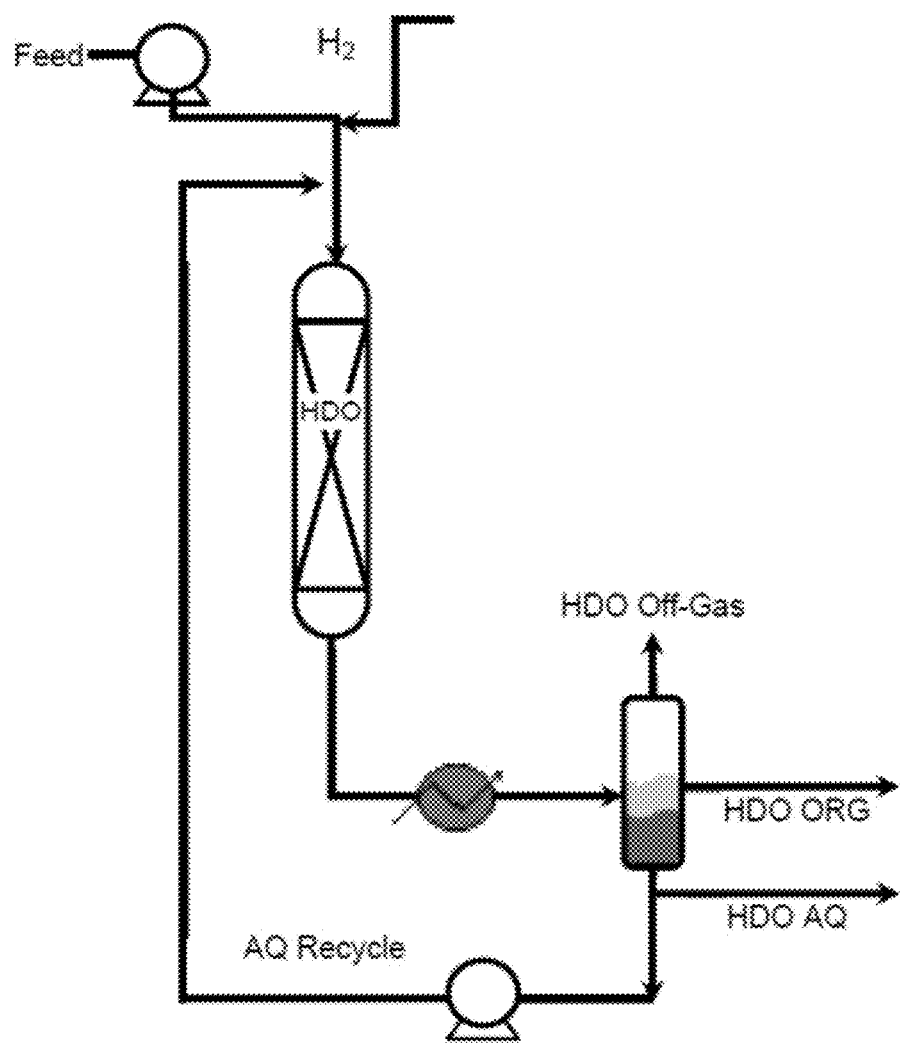

The present invention relates to catalysts and methods for producing monooxygenates, dioxygenates, ketones, carboxylic acids, cyclic ethers, aldehydes, and alcohols from biomass-derived oxygenated hydrocarbons using catalysts containing palladium, molybdenum, tin, and tungsten. Alternatively, the catalyst contains a Group VIII transition metal (i.e., Pd, Pt, Ni, Co, Rh, Ir, Ru, Fe, Os, etc.), molybdenum, tin, and tungsten on an acidic support. Exemplary embodiments of the general process—referred to as hydrodeoxygenation (HDO)—are illustrated in FIGS. 1A and 1B. A feedstock solution containing an oxygenated hydrocarbon is reacted with hydrogen over a heterogeneous HDO catalyst to produce oxygenated compounds having a lower molecular weight than the starting oxygenated hydrocarbons. The oxygenated compounds produced are useful as industrial chemicals or chemical intermediates for the production of liquid fuels and chemicals. The hydrogen may originate from any external source, be generated in-situ, or be derived from a parallel APR process. The hydrogen and oxygenated hydrocarbons may also be supplemented with recycled hydrogen and oxygenated hydrocarbons derived from the process. Unless otherwise indicated, the following terms shall be defined herein as indicated below.

The term "biomass" refers to, without limitation, organic materials produced by plants (such as leaves, roots, seeds and stalks), and microbial and animal metabolic wastes. Common biomass sources include: (1) agricultural residues, including corn stover, straw, seed hulls, sugarcane leavings, bagasse, nutshells, cotton gin trash, and manure from cattle, poultry, and hogs; (2) wood materials, including wood or bark, sawdust, timber slash, and mill scrap; (3) municipal solid waste, including recycled paper, waste paper and yard clippings; (4) algae-derived biomass, including carbohydrates and lipids from microalgae (e.g., *Botryococcus braunii, Chlorella, Dunaliella tertiolecta, Gracilaria, Pleurochyrsis camerae*, and *Sargassum*) and macroalgae (e.g., seaweed); and (5) energy crops, including poplars, willows, switch grass, *miscanthus*, sorghum, alfalfa, prairie bluestream, corn, soybean, and the like. The term also refers to the primary building blocks of the above, namely, lignin, cellulose, hemicellulose and carbohydrates, such as saccharides, sugars and starches, among others.

The term "oxygenated hydrocarbon" refers to carbohydrates (e.g., monosaccharides, disaccharides, oligosaccharides, polysaccharides, and starches), sugars (e.g., glucose, sucrose, xylose, etc.), sugar alcohols (e.g., diols, triols, and polyols), and sugar degradation products (e.g., hydroxymethyl furfural (HMF), levulinic acid, formic acid, and furfural).

The term "Group VIII" transition metal refers to an element selected from the group consisting of: Fe, Co, Ni, Ru, Rh, Pd, Os, Ir, and Pt, in any oxidation state.

The term "Group VIIB" transition metal refers to an element selected from the group consisting of Mn, Tc, and Re, in any oxidation state.

The term "monooxygenates" refers to a hydrocarbon molecule containing two or more carbon atoms and one oxygen atom.

The term "dioxygenates" refers to a hydrocarbon molecule containing two or more carbon atoms and two oxygen atoms.

The term "polyoxygenates" refers to a hydrocarbon molecule containing two or more carbon atoms and three or more oxygen atoms.

The term "bioreforming" refers to, without limitation, processes for catalytically converting biomass and other carbohydrates to lower molecular weight hydrocarbons and oxygenated compounds, such as alcohols, ketones, cyclic ethers, esters, carboxylic acids, aldehydes, dioxygenates, and other polyoxygenated hydrocarbons, using aqueous phase reforming, hydrogenation, hydrogenolyis, hydrodeoxygenation and/or other conversion processes involving the use of heterogeneous catalysts. Bioreforming also includes the further catalytic conversion of such lower molecular weight oxygenated compounds to $C_{4+}$ compounds.

Feedstocks

Feedstocks useful in the present invention may originate from any source, but are preferably derived from biomass. Biomass generally includes three major components: Cellulose, a primary sugar source for bioconversion processes, includes high molecular weight polymers formed of tightly linked glucose monomers; Hemicellulose, a secondary sugar source, includes shorter polymers formed of various sugars; and Lignin, which includes phenylpropanoic acid moieties polymerized in a complex three dimensional structure. For lignocellulosic biomass, the overall composition will vary based on plant variety or type and is roughly 40-50% cellulose, 20-25% hemicellulose, and 25-35% lignin, by weight percent. This composition can be deconstructed using any one or more methods, including the following, either alone or in combination: (1) thermochemical treatment using mineral acid, strong base, water at autohydrolysis conditions, gas catalyst, oxidation catalyst, and/or an organic solvent (2) enzymatic hydrolysis, and more recently (3) catalytic biomass deconstruction. Regardless of the process used, the resulting deconstruction product is likely to contain the desired oxygenated hydrocarbons suitable for use in the present invention.

The feedstocks may be pure materials, purified mixtures, or raw materials such as sugars and starches derived from the processing of corn, sugarcane, beet sugars, rice, wheat, algae, or energy crops. Some applicable feedstocks are also commercially available and may be obtained as by-products from other processes, such as glycerol from biodiesel fuel production. The feedstocks can also be intermediates formed as part of a larger process or in the same process, such as sugar alcohols produced in the initial stage of sugar hydrogenation.

In addition to the oxygenated hydrocarbons, the feedstock may also include lignin, one or more extractives, one or more ash components, or one or more organic products (e.g., lignin derivatives). Extractives will typically include terpenoids, stilbenes, flavonoids, phenolics, aliphatics, lignans, alkanes, proteinaceous materials, and other inorganic products. Ash components will typically include Al, Ba, Ca, Fe, K, Mg, Mn, P, S, Si, Zn, etc. Other organic products will typically include 4-ethyl phenol, 4-ethyl-2-methoxy phenol, 2-methoxy-4-propyl phenol, vanillin, 4-propyl syringol, vitamin E, steroids, long chain hydrocarbons, long chain fatty acids, stilbenoids, etc.

In general, the feedstock includes any oxygenated hydrocarbon having three or more carbon atoms and an oxygen-to-carbon ratio of between about 0.5:1 to about 1:1.2. In one aspect, the oxygenated hydrocarbon has 3 to 12 carbon atoms or 3 to 6 carbon atoms. In another aspect, the oxygenated hydrocarbon has more than 12 carbon atoms. Non-limiting examples of preferred oxygenated hydrocarbons include monosaccharides, disaccharides, trisaccharides, polysaccharides, oligosaccharides, sugars, sugar alcohols, sugar degradation products, alditols, hemicelluloses, cellulosic derivatives, lignocellulosic derivatives, starches, organic acids, polyols, and the like. Preferably, the oxygenated hydrocarbon includes polysaccharides, oligosaccharides, trisaccharides, disaccharides, monosaccharides, sugar, sugar alcohols, sugar degradation products, and other polyhydric alcohols. More preferably, the oxygenated hydrocarbon is a trisaccharide, a disaccharide, a sugar, such as glucose, fructose, sucrose, maltose, lactose, mannose or xylose, or a sugar alcohol, such as arabitol, erythritol, glycerol, isomalt, lactitol, maltitol, mannitol, sorbitol, xylitol, arabitol, or glycol. The oxygenated hydrocarbons may also include alcohols derived by the hydrogenation of the foregoing.

Alternatively, the feedstock may include oxygenated hydrocarbons solvated by a solvent. Non-limiting examples of solvents include: organic solvents, such as ionic liquids, acetone, ethanol, 4-methyl-2-pentanone, and other oxygenated hydrocarbons; dilute acids, such as acetic acid, oxalic acid, hydrofluoric acid; bioreforming solvents; and water. The solvents may be from external sources, recycled, or generated in-situ, such as in-situ generated oxygenated compounds (e.g. $C_{2+} O_{2+}$ oxygenated hydrocarbons).

Production of Oxygenated Compounds

The oxygenated compounds are prepared by reacting hydrogen with an aqueous feedstock solution containing water and the oxygenated hydrocarbons over an HDO catalyst containing palladium, molybdenum, tin, and tungsten. The HDO catalyst may also contain another Group VIII transition metal (i.e., Pt, Ni, Co, Rh, Ir, Ru, Fe, Os, etc.) as a substitute or supplement for the palladium, and/or may be disposed on an acidic support. The HDO catalyst may be referred to as Pd:Mo:Sn throughout the specification, but it should be understood that the reference is intended to include the use of other Group VIII transition metals as alternatives or supplements to palladium.

The hydrogen may be generated in-situ using aqueous phase reforming (in-situ-generated $H_2$ or APR $H_2$), or a combination of APR $H_2$, external $H_2$ or recycled $H_2$, or just simply external $H_2$ or recycled $H_2$. The term "external $H_2$" refers to hydrogen that does not originate from the feedstock solution, but is added to the reactor system from an external source. The term "recycled $H_2$" refers to unconsumed hydrogen, which is collected and then recycled back into the reactor system for further use. External $H_2$ and recycled $H_2$ may also be referred to collectively or individually as "supplemental $H_2$." In general, supplemental $H_2$ may be added for purposes of supplementing the APR hydrogen, or to increase the reaction pressure within the system, or to increase the molar ratio of hydrogen to carbon and/or oxygen in order to enhance the production yield of certain reaction product types, such as ketones and alcohols.

The oxygenate compounds are prepared by catalytically reacting the aqueous feedstock solution containing water and the oxygenated hydrocarbons in the presence of a Pd:Mo:Sn HDO catalyst at a temperature and pressure to produce the desired oxygenate compounds. The Pd:Mo:Sn HDO catalyst is a heterogeneous catalyst containing a combination of palladium, molybdenum, and tin whether alloyed or admixed in combination. The HDO catalyst may also contain another Group VIII transition metal (i.e., Pt, Ni, Co, Rh, Ir, Ru, Fe, Os, etc.) as a substitute or supplement for the palladium. Loading of the palladium or other Group VIII transition metal is in the range of about 0.05 wt % to about 5 wt %, with weight percentages of 0.01% and 0.05% increments between, such as 0.075%, 0.10%, 0.20%, 0.50%, 0.75%, 1.00%, 1.10%, 1.15%, 2.00%, 2.50%, 5.00%, etc. Loading of the molybdenum is in the range of about 0.05 wt % to about 10 wt %, with weight percentages of 0.01% and 0.05% increments between, such as 0.075%, 0.10%, 0.20%, 0.50%, 0.75%, 1.00%, 1.10%, 1.15%, 2.00%, 2.50%, 5.00%, 6.00%, 8.50%, 10.0%, etc. Loading of the tin is in the range of about 0.0125 wt % to about 5 wt %, with weight percentages of 0.01% and 0.05% increments between, such as 0.025%, 0.050%, 0.075%, 0.10%, 0.20%, 0.50%, 0.75%, 1.00%, 1.10%, 1.15%, 2.00%, 2.50%, 5.00%, etc.

The preferred atomic ratio of the palladium to molybdenum is in the range of about 0.25-to-1 to 10-to-1, including any ratios between, such as 0.50, 1.00, 2.50, 5.00, and 7.50-to-1. The preferred atomic ratio of the tin to molybdenum is in the range of about 0.125-to-1 to 10-to-1, including any ratios between, such as 0.50, 1.00, 2.50, 5.00, and 7.50-to-1. The preferred atomic ratio of the palladium to tin is in the range of about 0.125-to-1 to 10-to-1, including any ratios between, such as 0.50, 1.00, 2.50, 5.00, and 7.50-to-1. If an alternative Group VIII transition metal is employed, the preferred atomic ratio would be that of palladium above. Preferably, the catalyst is adhered to a tungsten-modified support, and the combination of the catalyst materials is from about 0.30 wt % to 18 wt % of the support. More preferably, the catalyst is adhered to a tungsten-modified acidic support, and the combination of the catalyst materials is from about 0.30 wt % to 18 wt % of the support.

In various embodiments above, the catalyst system includes a support suitable for suspending the HDO catalyst in the feedstock solution. The support should be one that provides a stable platform for the HDO catalyst and reaction conditions. The support may take any form that is stable at the chosen reaction conditions to function at the desired levels, and specifically stable in aqueous feedstock solutions. Such supports include, without limitation, nitride, carbon, silica, alumina, zirconia, titania, vanadia, ceria, boron nitride, heteropolyacid, kieselguhr, hydroxyapatite, zinc oxide, chromia, zeolites, tungstated zirconia, titania zirconia, sulfated zirconia, phosphated zirconia, acidic alumina, silica-alumina, sulfated alumina, iron aluminate, phosphated alumina, theta alumina, niobia, niobia phosphate, oxides of the foregoing, and mixtures thereof. Nanoporous supports such as zeolites, carbon nanotubes, or carbon fullerene may also be used.

One catalyst support is zirconia. The zirconia may be produced via precipitation of zirconium hydroxide from zirconium salts, through sol-gel processing, or any other method. The zirconia is preferably present in a crystalline form achieved through calcination of the precursor material at temperatures exceeding 400° C., and may include both tetragonal and monoclinic crystalline phases. A modifying agent may be added to improve the textural or catalytic properties of the zirconia. Such modifying agents include, without limitation, sulfate, tungstenate, phosphate, titania, silica, and oxides of Group IIIB metals, especially Ce, La, or Y. In one embodiment, the catalyst includes Pd, Mo and Sn on tungsten-modified monoclinic zirconia. In another embodiment, the catalyst includes Pd, Mo, and Sn on tungsten-modified tetragonal zirconia.

The tungstated zirconia may be produced via impregnation of zirconium hydroxide with an aqueous solution containing a tungsten salt, precipitation from zirconium and tungsten salts through sol-gel processing, or any other method. The tungstated zirconia is preferably present in a mixed oxide crystalline form achieved through calcination of the precursor material at temperatures exceeding 400° C., preferentially above 600° C., and may include both tetragonal and monoclinic crystalline zirconia phases as well as polytungsten oxide clusters present on the catalyst support surface. A modifying agent may be added to improve the textural or catalytic properties of the tungstated zirconia. Such modifying agents include, without limitation, tungstenate, sulfate, phosphate, titania, silica, and oxides of Group IIIB metals, especially Ce, La, or Y. In one embodiment, the catalyst includes Pd, Mo and Sn on tungstated zirconia.

Another catalyst support is tungsten oxide. Tungsten oxide may be prepared via precipitation from a tungsten-containing salt, or other methods.

Another catalyst support is niobia phosphate. Niobia phosphate may be produced via precipitation from niobium- and phosphate-containing salts through sol-gel processing, impregnation of an aqueous solution of a phosphate solution onto niobium oxide, or other methods.

Yet another catalyst support is titania. The titania may be produced via precipitation from titanium salts, through sol-gel processing, or any other method. The titania is preferably present in a crystalline form and may include both anatase and rutile crystalline phases. A modifying agent may be added to improve the textural or catalytic properties of the titania. Such modifying agents include, without limitation, sulfate, silica, tungstenate, and oxides of Group IIIB metals, especially Ce, La, or Y.

Another catalyst support is a transitional alumina, preferentially theta alumina. The theta alumina may be produced via precipitation from aluminum salts, through sol-gel processing, or any other method. Preferably, the support would be manufactured through peptization of a suitable aluminum hydroxide, preferentially bohemite or pseudo-bohemite, with nitric acid in the presence of an organic binder, preferentially hydroxyethyl cellulose. After forming, the support must then be calcined to a final temperature between about 900° C. to about 1200° C., preferentially greater than 1000° C. A modifying agent may be added to improve the textural or catalytic properties of the alumina. Such modifying agents include, without limitation, sulfate, silica, Fe, Ce, La, Cu, Co, Mo, or W.

The support may also be treated or modified to enhance its properties. For example, the support may be treated, as by surface-modification, to modify surface moieties, such as hydrogen and hydroxyl. Surface hydrogen and hydroxyl groups can cause local pH variations that affect catalytic efficiency. The support may also be modified, for example, by treating it with sulfates, phosphates, tungsten, silanes, lanthanides, alkali compounds or alkali earth compounds.

Conventional methods for preparing catalyst systems are well known in the art. Common methods include incipient wetting, evaporative impregnation, chemical vapor deposition, wash-coating, magnetron sputtering techniques, and the like. The method chosen to fabricate the HDO catalyst is not critical to the function of the invention, with the proviso that different catalysts and methods of preparation will yield different results, depending upon considerations such as overall surface area, porosity, etc.

The catalyst may also be prepared using a high ionic strength impregnation solution. The high ionic strength impregnation solution may include an inorganic agent such as ammonium nitrate, ammonium citrate, ammonium chloride, ammonium acetate, or other volatile/combustible salts. The inorganic agent is subsequently removed prior to the HDO catalytic reaction. Using a high ionic strength impregnation solution improves the distribution of the metal catalytic components on the support.

To produce the oxygenated compounds, the oxygenated hydrocarbon is combined with water to provide an aqueous feedstock solution having a concentration effective for causing the formation of the desired reaction products. The water-to-carbon ratio on a molar basis is preferably from about 0.5:1 to about 100:1, including ratios such as 1:1, 2:1, 3:1, 4:1, 5:1, 6:1, 7:1, 8:1, 9:1, 10:1, 15:1, 25:1, 50:1 75:1, 100:1, and any ratios there-between. The feedstock solution may also be characterized as a solution having at least about 1.0 weight percent (wt %) of the total solution as an oxygenated hydrocarbon. For instance, the solution may include one or more oxygenated hydrocarbons, with the total concentration of the oxygenated hydrocarbons in the solution being at least about 1%, 5%, 10%, 20%, 30%, 40%, 50%, 60%, 70%, 80% or greater by weight, including any percentages between, and depending on the oxygenated hydrocarbons used. In one embodiment, the feedstock solution includes at least about 10%, 20%, 30%, 40%, 50%, or 60% of a sugar, such as glucose, fructose, sucrose or xylose, or a sugar alcohol, such as sorbitol, mannitol, glycerol or xylitol, by weight. Water-to-carbon ratios and percentages outside of the above stated ranges are also included.

The feedstock solution is reacted with hydrogen in the presence of the Pd:Mo:Sn HDO catalyst at temperatures, pressures, and weight hourly space velocities effective to produce the desired oxygenated compounds. The specific oxygenates produced will depend on various factors, including the feedstock solution, reaction temperature, reaction pressure, water concentration, hydrogen concentration, the reactivity of the catalyst, and the flow rate of the feedstock solution as it affects the space velocity (the mass/volume of reactant per unit of catalyst per unit of time), gas hourly space velocity (GHSV), and weight hourly space velocity (WHSV). For example, an increase in flow rate, and thereby a reduction of feedstock exposure to the HDO catalyst over time, will limit the extent of the reactions that may occur, thereby causing increased yield for higher level di- and tri-oxygenates, with a reduction in ketone, alcohol, and cyclic ether yields.

The reaction temperature and pressures are preferably selected to maintain at least a portion of the feedstock in the liquid phase at the reactor inlet. It is recognized, however, that temperature and pressure conditions may also be selected to more favorably produce the desired products in the vapor-phase. In general, the reaction should be conducted at process conditions wherein the thermodynamics of the proposed reaction are favorable. For instance, the minimum pressure required to maintain a portion of the feedstock in the liquid phase will likely vary with the reaction temperature. As temperatures increase, higher pressures will generally be required to maintain the feedstock in the liquid phase, if desired. Pressures above that required to maintain the feedstock in the liquid phase (i.e., vapor-phase) are also suitable operating conditions.

In general, the reaction may include a temperature gradient to allow partial deoxygenation of the oxygenated hydrocarbon feedstock at temperatures below the caramelization point of the feedstock. Including a temperature gradient helps prevent the oxygenated hydrocarbons in the feedstock from condensing (e.g., caramelizing) on the catalyst and creating a substantial pressure drop across the reactor which can lead to inoperability of the reactor. The caramelization point, and therefore the required temperature gradient, will vary depending on the feedstock. In one embodiment, the temperature gradient is from about 170° C. to 300° C. or between about 200° C. to 290° C. In another embodiment, a temperature gradient is not employed.

Operating pressures up to about 2000 psig can be used to help maintain the carbon backbone and minimize the amount of light organic acids and ketones that are formed by increasing the product selectivity towards alcohols. By increasing operating pressures, the thermodynamics of the reaction favor alcohols to ketones and organic acids, thereby shifting the product selectivity, maintaining the carbon backbone, and improving product yields. Light organic acids are particularly undesirable products as they are highly corrosive. Producing fewer light organic acids provides more flexibility with regards to materials of construction of a reactor system because corrosion is less of an issue.

In condensed phase liquid reactions, the pressure within the reactor must be sufficient to maintain the reactants in the condensed liquid phase at the reactor inlet. For liquid phase reactions, the reaction temperature should be greater than about 100° C., or 120° C., or 150° C., or 180° C., or 200° C., and less than about 300° C., or 290° C., or 270° C., or 250° C., or 220° C. The reaction pressure should be greater than about 70 psig, or 145 psig, or 300 psig, or 500 psig, or 750 psig, or 1050 psig, and less than about 2000 psig, or 1950 psig, or 1900 psig, or 1800 psig. In one embodiment, the reaction temperature is between about 120° C. and 300° C., or between about 200° C. and 300° C., or between about 270° C. and 290° C., and the reaction pressure is between about 145 and 1950 psig, or between about 1000 and 1900 psig, or between about 1050 and 1800 psig.

For vapor phase reactions, the reaction should be carried out at a temperature where the vapor pressure of the oxygenated hydrocarbon is at least about 0.1 atm, preferably higher (e.g., 350 psi), and the thermodynamics of the reaction are favorable. This temperature will vary depending upon the specific oxygenated hydrocarbon compound used, but is generally greater than about 100° C., or 120° C., or 250° C., and less than about 600° C., or 500° C., or 400° C. for vapor phase reactions. In one embodiment, the reaction temperature is between about 120° C. and about 500° C., or between about 250° C. and about 400° C.

In general, the reaction should be conducted under conditions where the residence time of the feedstock solution over the catalyst is appropriate to generate the desired products. For example, the WHSV for the reaction may be at least about 0.01 gram of oxygenated hydrocarbon per gram of catalyst per hour, and more preferably the WHSV is about 0.01 to 40.0 g/g hr, including a WHSV of about 0.01, 0.025, 0.05, 0.075, 0.1, 0.25, 0.5, 0.75, 1.0, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 6, 7, 8, 9, 10, 11, 12, 13, 14, 15, 20, 25, 30, 35, 40 g/g hr, and ratios between (including 0.77, 0.78, 0.79, 2.61, 2.62, 2.63, etc.).

The hydrogen used in the reaction is preferably external hydrogen, but may include small amounts of in-situ generated hydrogen. The amount (moles) of external hydrogen or recycled hydrogen introduced to the feedstock may be between about 0-1200%, 5-1200%, 10-1200%, 15-1200%, 20-1200%, 25-1200%, 30-1200%, 35-1200%, 40-1200%, 45-1200%, 50-1200%, 55-1200%, 60-1200%, 65-1200%, 70-1200%, 75-1200%, 80-1200%, 85-1200%, 90-1200%, 95-1200%, 98-1200%, 100-1200%, 200-1200%, 300-1200%, 400-1200%, 500-1200%, 600-1200%, 700-1200%, 800-1200%, 900-1200%, 1000-1200%, 1100-1200%, or 1150-1200% of the total number of moles of the oxygenated hydrocarbon(s) in the feedstock, including all intervals between. When the feedstock solution, or any portion thereof, is reacted with in-situ generated hydrogen and external hydrogen or recycled hydrogen, the molar ratio of in-situ generated hydrogen to external hydrogen (or recycled hydrogen) is at least 1:100, 1:50, 1:20; 1:15, 1:10, 1:5; 1:3, 1:2, 1:1, 2:1, 3:1, 5:1, 10:1, 15:1, 20:1, 50:1, 100:1 and ratios between (including 4:1, 6:1, 7:1, 8:1, 9:1, 11:1, 12:1, 13:1, 14:1, 15:1, 16:1, 17:1, 18:1 and 19:1, and vice-versa).

Catalyst Selection

One unique aspect of the present invention is the ability of the Pd:Mo:Sn HDO catalyst to effectively convert oxygenated hydrocarbons to the desired oxygenated compounds using external hydrogen without the feedstock saturating into alkanes or condensing oxygenated hydrocarbons on the catalyst. The catalyst composition, catalyst support, and operating conditions (e.g., temperature, pressure, WHSV) are carefully chosen to minimize these unwanted side reactions that can lead to lower yields and/or inoperability of the process due to a variety of factors including the creation of an unwanted pressure drop within the reactor.

Another unique aspect of the present invention is the ability of the Pd:Mo:Sn HDO catalyst to effectively convert oxygenated hydrocarbons to the desired compounds in the presence of lignin, extractives, ash components, and other inorganic and organic compounds that can limit catalyst selectivity and activity.

These characteristics can minimize the need for regeneration and the time between regeneration and production of oxygenated compounds.

HDO Recycle Stream

Recycle streams may be used to maximize product yields and reduce catalyst deactivation. The product of the HDO reaction includes partially deoxygenated hydrocarbons. Partially deoxygenated hydrocarbons include $C_{2+}O_{2+}$ hydrocarbons (e.g., disaccharides, monosaccharides, sugars, sugar alcohols, alditols, heavy organic acids, and heavy diols, triols, and other polyols). Recycling these partially deoxygenated hydrocarbons back into the HDO reactor system reduces the carbohydrate concentration entering the HDO reactor system by diluting the carbohydrate-rich feedstock solution with partially deoxygenated hydrocarbons. Diluting the highly reactive carbohydrate feedstream minimizes condensation reactions in the HDO reactor system in which the feedstock condenses on the Pd:Mo:Sn HDO catalyst, fouling the catalyst, and requiring frequent catalyst changes and/or regeneration. The preferred recycle to fresh feed weight ratio is in the range of about 0.25-to-1 to 10-to-1, including any ratios between, such as about 0.50, 1.00, 2.50, 4.00, 5.00, and 7.50-to-1.

Catalyst Regeneration

While the catalysts described herein possess certain characteristics that limit fouling, the potential for carbonaceous deposits to develop through unwanted side reactions still exists. As these deposits accumulate, access to the catalytic sites on the surface becomes restricted and the catalyst performance declines, resulting in lower conversion and yields to desired products. The catalysts described herein may be regenerated to remove carbonaceous deposits that form on the catalyst during the HDO reaction. The catalysts may be subjected to either oxidative or reductive regeneration to remove the carbon-containing species from the catalyst surface. Oxidative regeneration is carried out by heating the HDO catalyst in the presence of oxygen to break C—O and C—C linkages in the carbonaceous deposits resulting in the release of CO and $CO_2$. The CO and $CO_2$ released from the catalyst can be separated and collected downstream. The amount of $CO_2$ in the regeneration stream can be used to monitor the status of regeneration—with a decrease in $CO_2$ to an insignificant amount indicating that regeneration of the catalyst is complete. Alternatively, reductive regeneration can be used to remove the carbon-containing species from the catalyst surface. Reductive catalyst regeneration can be accomplished by heating the catalyst in the presence of hydrogen to break C—O and C—C linkages in the carbonaceous deposits, resulting in the production of alkanes (e.g., $CH_4$, $C_2H_6$, $C_3H_8$, $C_4H_{10}$, $C_5H_{12}$, $C_6H_{14}$, etc.). Similar to the oxidative regeneration described above, measuring the amount of alkanes emitted is an effective means for monitoring the regeneration status.

Reactor System

The reactions described herein may be carried out in any reactor of suitable design, including continuous-flow, batch, semi-batch or multi-system reactors, without limitation as to design, size, geometry, flow rates, etc. The reactor system may also use a fluidized catalytic bed system, a swing bed system, fixed bed system, a moving bed system, or a combination of the above. Preferably, the present invention is practiced utilizing a continuous-flow system at steady-state equilibrium.

FIGS. 1A and 1B are schematic illustrations showing processes (FIG. 1B includes an aqueous recycle stream) for converting a biomass-derived oxygenated hydrocarbon feedstock solution to a final desired product using a single reactor containing a Pd:Mo:Sn HDO catalyst on a support. The feedstock solution includes a solvent (e.g., water, recycled partially deoxygenated hydrocarbons, etc.) combined with one or more oxygenated hydrocarbons, such as carbohydrates (e.g., monosaccharides, disaccharides, oligosaccharides, polysaccharides, and starches), sugars (e.g., glucose, sucrose, xylose, etc.), sugar alcohols (e.g., diols, triols, and polyols), and sugar degradation products (e.g., hydroxymethyl furfural (HMF), levulinic acid, formic acid, and furfural). The feedstock is fed via a pump to the HDO reactor system having the Pd:Mo:Sn HDO catalyst on a support, where it subsequently reacts with hydrogen to generate the desired products (e.g., monooxygenates, dioxygenates, ketones, carboxylic acids, cyclic ethers, aldehydes, and alcohols).

The effluent stream from the reactor contains a mixture of water, hydrogen, carbon dioxide, light hydrocarbons (e.g., alkanes have four or fewer carbon atoms, such as methane, ethane, propane, and butane), monooxygenates, dioxygenates, alcohols, ketones, carboxylic acids, aldehydes, cyclic ethers, and unreacted feedstock. The mixture is passed through a three-phase separator to separate the non-condensed gases (such as hydrogen, carbon dioxide, methane, ethane, and propane) from the HDO organic products stream and the HDO aqueous stream. The non-condensed gases are removed via an HDO off-gas stream. The non-condensable stream can be either combusted to create process heat (i.e., heat for driving the reaction in the HDO reactor), or sent to a separation system where hydrogen can be recovered for recycle back to the hydrogen stream. The HDO aqueous stream, containing partially deoxygenated hydrocarbons, may be recycled back to the reactor inlet. An HDO aqueous stream, including some monooxygenates (e.g., alcohols), serves to prevent a build-up of water in the reactor system.

Condensation

Figure 2:
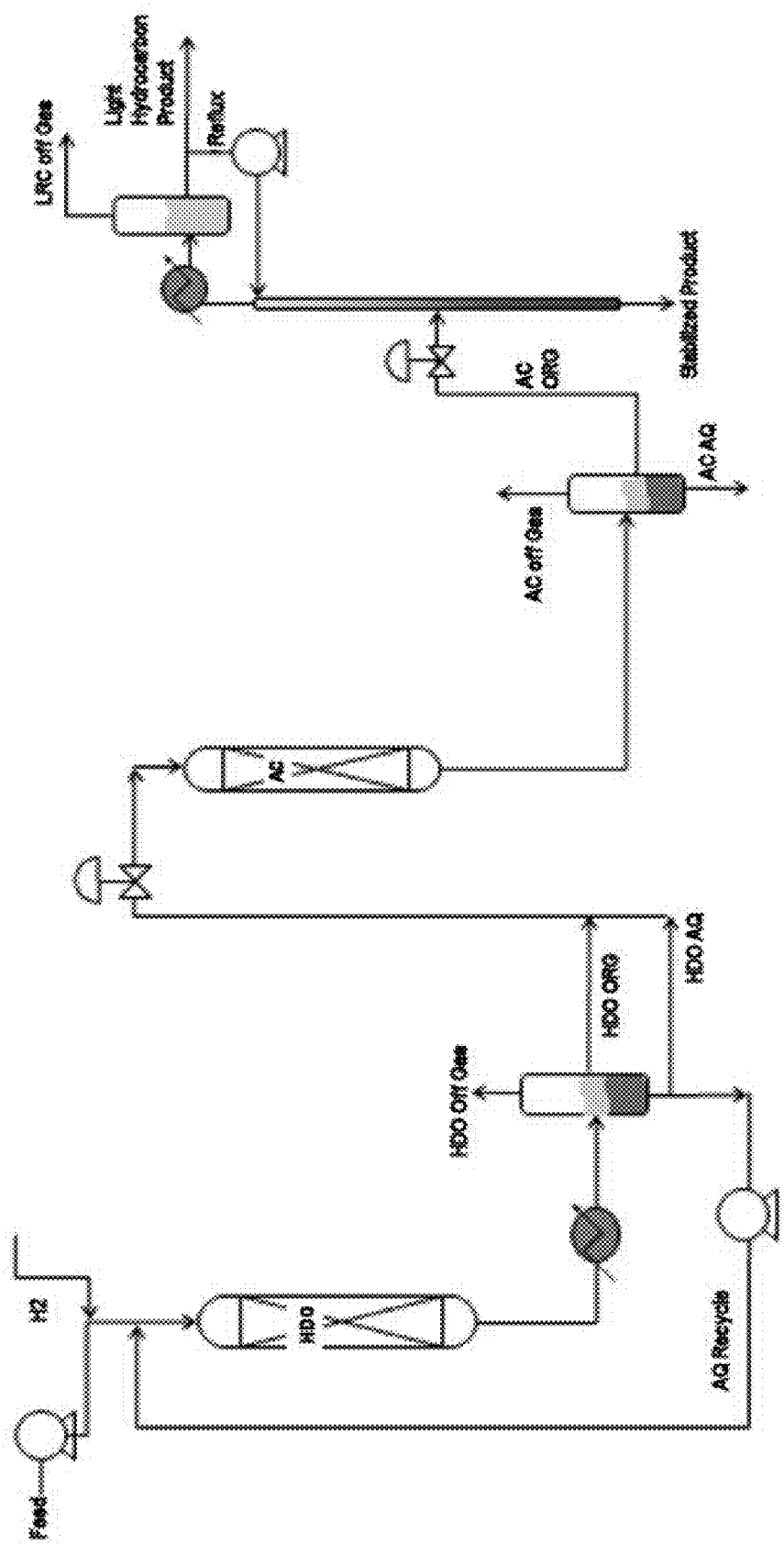
FIG. 2 is a flow diagram illustrating an embodiment of the present invention for producing chemicals and/or gasoline from biomass-derived feedstocks.

FIG. 2 is a schematic illustration showing one process for converting a biomass-derived oxygenated hydrocarbon feedstock solution to a fuel product (e.g., gasoline, diesel, or jet fuel), chemical product, or chemical intermediate using an HDO reactor containing a Pd:Mo:Sn HDO catalyst on a support, a condensation reactor, and various recycle streams. The feedstock solution includes a solvent (e.g., water, recycled partially deoxygenated hydrocarbons, etc.) combined with one or more oxygenated hydrocarbons, such as carbohydrates (e.g., monosaccharides, disaccharides, oligosaccharides, polysaccharides, and starches), sugars (e.g., glucose, sucrose, xylose, etc.), sugar alcohols (e.g., diols, triols, and polyols), and sugar degradation products (e.g., hydroxymethyl furfural (HMF), levulinic acid, formic acid, and furfural). The feedstock is fed via a pump to the HDO reactor system having the Pd:Mo:Sn HDO catalyst on an acidic support, where it subsequently reacts with hydrogen to generate intermediate products in an effluent stream.

The effluent stream from the HDO reactor contains a mixture of solvent (e.g., water), hydrogen, carbon dioxide, light hydrocarbons, monooxygenates, dioxygenates, alcohols, ketones, carboxylic acids, aldehydes, cyclic ethers, and unreacted feedstock. The mixture is passed through a three-phase separator to separate the non-condensed gases (e.g., hydrogen, carbon dioxide, methane, ethane and propane) from the HDO organic products stream and the HDO aqueous stream. The non-condensed gases are removed via an HDO off-gas stream. The non-condensable stream can be either combusted to create process heat (i.e., heat for driving the reaction in the HDO reactor) or sent to a separation system where hydrogen can be recovered for recycle back to the HDO reactor. The HDO aqueous stream contains partially deoxygenated hydrocarbons. A portion of the HDO aqueous stream may be recycled back to the reactor inlet.

A combination of the HDO organic products stream and the HDO aqueous stream is fed to a condensation reactor (e.g., acid condensation (AC)) such as the system described in International Patent No. WO 2008/109877 to Cortright et al., which is herein incorporated by reference. A condensation reactor bed is configured to receive the HDO organic products and the HDO aqueous streams for contact with a condensation catalyst to produce $C_{4+}$ compounds.

The condensation catalyst will generally be a catalyst capable of forming longer chain compounds by linking two oxygen-containing species through a new carbon-carbon bond, and converting the resulting compound to a hydrocarbon, alcohol, or ketone. The condensation catalyst may include, without limitation, carbides, nitrides, zirconia, alumina, silica, aluminosilicates, phosphates, zeolites, titanium oxides, zinc oxides, vanadium oxides, lanthanum oxides, yttrium oxides, magnesium oxides, cerium oxides, barium oxides, calcium oxides, hydroxides, heteropolyacids, organic acids, acid modified resins, base modified resins, and combinations thereof. The condensation catalyst may include the above alone or in combination with a modifier, such as Ce, La, Y, Sc, P, B, Bi, Li, Na, K, Rb, Cs, Mg, Ca, Sr, Ba, and combinations thereof. The condensation catalyst may also include a metal, such as Cu, Ag, Au, Pt, Ni, Fe, Co, Ru, Zn, Cd, Ga, In, Rh, Pd, Ir, Re, Mn, Cr, Mo, W, Sn, Os, alloys and combinations thereof, to provide metal functionality. Exemplary condensation catalysts are also described in WO 2008/109877.

The condensation catalyst may be self-supporting (i.e., the catalyst does not need another material to serve as a support), or may require separate support suitable for suspending the catalyst in the reactant stream. Particularly beneficial supports include alumina, silica, and zirconia. In other embodiments, particularly when the condensation catalyst is a powder, the catalyst system may include a binder to assist in forming the catalyst into a desirable catalyst shape. Applicable forming processes include extrusion, pelletization, oil dropping, or other known processes. Zinc oxide, alumina, and a peptizing agent may also be mixed together and exruded to produce a formed material. After drying, this material is calcined at a temperature appropriate for formation of the catalytically active phase, which usually requires temperatures in excess of 350° C. Other catalyst supports may include those described in further detail below.

In one embodiment, the condensation reaction is performed using a catalyst having acidic functionality. The acid catalysts may include, without limitation, aluminosilicates (zeolites), silica-alumina phosphates (SAPO), aluminum phosphates (ALPO), amorphous silica alumina, zirconia, sulfated zirconia, tungstated zirconia, tungsten carbide, molybdenum carbide, titania, acidic alumina, phosphated alumina, phosphated silica, sulfated carbons, phosphated carbons, acidic resins, heteropolyacids, inorganic acids, and combinations thereof. In one embodiment, the catalyst may also include a modifier, such as Ce, La, Y, Li, Na, K, Rb, Cs, Mg, Ca, Sr, Ba, P, B, Bi, and combinations thereof. The catalyst may also be modified by the addition of a metal, such as Cu, Ag, Au, Pt, Ni, Fe, Co, Ru, Rh, Zn, Ga, In, Pd, Ir, Re, Mn, Cr, Mo, W, Sn, Os, alloys and combinations thereof, to provide metal functionality, and/or sulfides and oxides of Ti, Zr, V, Nb, Ta, Mo, Cr, W, Mn, Re, Al, Ga, In, Fe, Co, Ir, Ni, Si, Cu, Zn, Sn, P, and combinations thereof. Tungstated zirconia has been found to be a particularly useful catalyst for the present process, especially when modified with Cu, Pd, Ag, Pt, Ru, Ni, Sn and combinations thereof. The acid catalyst may be homogenous, self-supporting or adhered to any one of the supports further described below, including supports containing carbon, silica, alumina, zirconia, titania, vanadia, ceria, heteropolyacids, alloys and mixtures thereof.

For example, the condensation catalyst may be a zeolite catalyst. The term "zeolite" as used herein refers not only to microporous crystalline aluminosilicate, but also microporous crystalline metal-containing aluminosilicate structures, such as galloaluminosilicates and gallosilicates. In such instances, In, Zn, Fe, Mo, Ag, Au, Ni, P, Y, Ta, and lanthanides may be exchanged onto zeolites to provide the desired activity. Metal functionality may be provided by metals such as Cu, Ag, Au, Pt, Ni, Fe, Co, Ru, Zn, In, Rh, Pd, Ir, Re, Mn, Cr, Mo, W, Sn, Os, alloys and combinations thereof.

Examples of suitable zeolite catalysts include ZSM-5, ZSM-11, ZSM-12, ZSM-22, ZSM-23, ZSM-35 and ZSM-48. Zeolite ZSM-5, and the conventional preparation thereof, is described in U.S. Pat. Nos. 3,702,886; Re. 29,948 (highly siliceous ZSM-5); U.S. Pat. Nos. 4,100,262 and 4,139,600, all incorporated herein by reference. Zeolite ZSM-11, and the conventional preparation thereof, is described in U.S. Pat. No. 3,709,979, which is also incorporated herein by reference. Zeolite ZSM-12, and the conventional preparation thereof, is described in U.S. Pat. No. 3,832,449, incorporated herein by reference. Zeolite ZSM-23, and the conventional preparation thereof, is described in U.S. Pat. No. 4,076,842, incorporated herein by reference. Zeolite ZSM-35, and the conventional preparation thereof, is described in U.S. Pat. No. 4,016,245, incorporated herein by reference. Another preparation of ZSM-35 is described in U.S. Pat. No. 4,107,195, the disclosure of which is incorporated herein by reference. ZSM-48, and the conventional preparation thereof, is taught by U.S. Pat. No. 4,375,573, incorporated herein by reference. Other examples of zeolite catalysts are described in U.S. Pat. No. 5,019,663 and U.S. Pat. No. 7,022,888, also incorporated herein by reference. In one embodiment, the condensation catalyst is a ZSM-5 zeolite modified with Cu, Pd, Ag, Pt, Ru, Ni, Sn, or combinations thereof.

As described in U.S. Pat. No. 7,022,888, the condensation catalyst may be a bifunctional pentasil zeolite catalyst including at least one metallic element from the group of Cu, Ag, Au, Pt, Ni, Fe, Co, Ru, Zn, Cd, In, Rh, Pd, Ir, Re, Mn, Cr, Mo, W, Sn, Os, alloys and combinations thereof, or a modifier from the group of In, Zn, Fe, Mo, Au, Ag, Y, Sc, Ni, P, Ta, lanthanides, and combinations thereof. The zeolite preferably has strong acidic sites, and may be used with reactant streams containing and an oxygenated hydrocarbon at a temperature of below 580° C. The bifunctional pentasil zeolite may have ZSM-5, ZSM-8 or ZSM-11 type crystal structure consisting of a large number of 5-membered oxygen-rings (i.e., pentasil rings). The zeolite with ZSM-5 type structure is a particularly preferred catalyst.

The condensation catalyst may include one or more zeolite structures comprising cage-like structures of silica-alumina. Zeolites are crystalline microporous materials with well-defined pore structures. Zeolites contain active sites, usually acid sites, which can be generated in the zeolite framework. The strength and concentration of the active sites can be tailored for particular applications. Examples of suitable zeolites for condensing secondary alcohols and alkanes may comprise aluminosilicates, optionally modified with cations, such as Ga, In, Zn, Mo, and mixtures of such cations, as described, for example, in U.S. Pat. No. 3,702,886, which is incorporated herein by reference. As recognized in the art, the structure of the particular zeolite or zeolites may be altered to provide different amounts of various hydrocarbon species in the product mixture. Depending on the structure of the zeolite catalyst, the product mixture may contain various amounts of aromatic and cyclic hydrocarbons.

Alternatively, solid acid catalysts such as alumina modified with phosphates, chloride, silica, and other acidic oxides could be used in practicing the present invention. Also, sulfated zirconia, phosphated zirconia, titania zirconia, or tungstated zirconia may provide the necessary acidity. Re and Pt/Re catalysts are also useful for promoting condensation of oxygenates to $C_{5+}$ hydrocarbons and/or $C_{5+}$ mono-oxygenates. The Re is sufficiently acidic to promote acid-catalyzed condensation. Acidity may also be added to activated carbon by the addition of either sulfates or phosphates.

The effluent stream from the condensation reactor contains a mixture of water, hydrogen, carbon dioxide, light hydrocarbons (e.g., alkanes having six or fewer carbon atoms), long chain alkanes (e.g., alkanes having greater than six carbon atoms), isoalkanes, napthenes, and aromatics (e.g., benzene, toluene, xylene, etc.). The condensation reactor effluent stream is passed through a three-phase separator to separate the condensation reactor off-gas from the condensation reactor organic products stream and the condensation reactor aqueous stream. The condensation reactor organic products stream can be further separated into fractions for liquid fuel compositions, such as a lighter $C_4$-$C_9$ fraction (primarily $C_4$-$C_9$, i.e., $C_4$, $C_5$, $C_6$, $C_7$, $C_8$, and $C_9$) for gasoline use, a moderate $C_7$-$C_{14}$ fraction (primarily $C_7$-$C_{14}$, i.e., $C_7$, $C_8$, $C_9$, $C_{10}$, $C_{11}$, $C_{12}$, $C_{13}$, and $C_{14}$) for kerosene use (e.g., jet fuel use), a heavier $C_{12}$-$C_{24}$ fraction (primarily $C_{12}$-$C_{24}$, i.e., $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, and $C_{24}$) for diesel fuel use, and a heaviest fraction ($C_{25+}$ and $C_{30+}$, i.e., $C_{25}$, $C_{26}$, $C_{27}$, $C_{28}$, $C_{29}$, $C_{30}$, $C_{31}$, $C_{32}$, $C_{33}$, $C_{34}$, $C_{35}$, etc.) for use as lubricants, fuel oils, or cracked to produce additional fractions.

$C_{4+}$ Compounds

The practice of the present invention results in the production of $C_{4+}$ alkanes, $C_{4+}$ alkenes, $C_{5+}$ cycloalkanes, $C_{5+}$ cycloalkenes, aryls, fused aryls, $C_{4+}$ alcohols, $C_{4+}$ ketones, $C_{4+}$ cyclic ethers, and mixtures thereof. The $C_{4+}$ alkanes and $C_{4+}$ alkenes have from 4 to 30 carbon atoms ($C_{4-30}$ alkanes and $C_{4-30}$ alkenes) and may be branched or straight chained alkanes or alkenes. The $C_{4+}$ alkanes and $C_{4+}$ alkenes may also include fractions of $C_{4-9}$, $C_{7-14}$, $C_{12-24}$ alkanes and alkenes, respectively, with the $C_{4-9}$ fraction directed to gasoline, the $C_{7-16}$ fraction directed to jet fuels, and the $C_{11-24}$ fraction directed to diesel fuel and other industrial applications. Examples of various $C_{4+}$ alkanes and $C_{4+}$ alkenes include, without limitation, butane, butene, pentane, pentene, 2-methylbutane, hexane, hexene, 2-methylpentane, 3-methylpentane, 2,2-dimethylbutane, 2,3-dimethylbutane, heptane, heptene, octane, octene, 2,2,4,-trimethylpentane, 2,3-dimethyl hexane, 2,3,4-trimethylpentane, 2,3-dimethylpentane, nonane, nonene, decane, decene, undecane, undecene, dodecane, dodecene, tridecane, tridecene, tetradecane, tetradecene, pentadecane, pentadecene, hexadecane, hexadecene, heptyldecane, heptyldecene, octyldecane, octyldecene, nonyldecane, nonyldecene, eicosane, eicosene, uneicosane, uneicosene, doeicosane, doeicosene, trieicosane, trieicosene, tetraeicosane, tetraeicosene, and isomers thereof.

The $C_{4+}$ cyclic ethers refers to, without limitation, saturated and unsaturated hetero-cyclic compounds having four or more carbon atoms wherein the hetero-atom is oxygen. The cyclic ethers of the present invention can be substituted or unsubstituted. The substituent group for both saturated and unsaturated substituted cyclic ethers includes the following moieties: alkyl, carbonyl, hydroxyl, alkoxyl, and combinations thereof. Cyclic ethers produced according to the present invention include: 2,5-dimethyl tetrahydrofuran, 2-ethyl tetrahydrofuran, 2-methyl tetrahydrofuran, 2,5-dimethyl furan, 2-methyl furan, tetrahydropyran, 2-methyl tetrahydropyran, 2-methanol tetrahydropyran, dihydro-5-methyl-5-(2-methylpropyl)-2(3H)-furanone, dihydro-5-pentyl-2(3H)-furanone, tetrahydro-2,2-dimethyl-5-(1-methylethyl)-furan, octahydro-2,2'-Bi-2H-pyran, 5-[(tetrahydro-2H-pyran-2-yl)oxy]-pentanal, 5-heptyldihydro-2(3H)-furanone, and 2-[(2-furanylmethoxy)methyl]tetrahydro-2H-pyran.

The $C_{5+}$ cycloalkanes and $C_{5+}$ cycloalkenes have from 5 to 30 carbon atoms and may be unsubstituted, mono-substituted or multi-substituted. In the case of mono-substituted and multi-substituted compounds, the substituted group may include a branched $C_{3+}$ alkyl, a straight chain $C_{1+}$ alkyl, a branched $C_{3+}$ alkylene, a straight chain $C_{2+}$ alkylene, a phenyl or a combination thereof. In one embodiment, at least one of the substituted groups include a branched $C_{3-12}$ alkyl, a straight chain $C_{1-12}$ alkyl, a branched $C_{3-12}$ alkylene, a straight chain $C_{1-12}$ alkylene, a straight chain $C_{2-12}$ alkylene, a phenyl or a combination thereof. In yet another embodiment, at least one of the substituted groups include a branched $C_{3-4}$ alkyl, a straight chain $C_{1-4}$ alkyl, a branched $C_{3-4}$ alkylene, straight chain $C_{1-4}$ alkylene, straight chain $C_{2-4}$ alkylene, a phenyl or a combination thereof. Examples of desirable $C_{5+}$ cycloalkanes and $C_{5+}$ cycloalkenes include, without limitation, cyclopentane, cyclopentene, cyclohexane, cyclohexene, methyl-cyclopentane, methyl-cyclopentene, ethyl-cyclopentane, ethyl-cyclopentene, ethyl-cyclohexane, ethyl-cyclohexene, propyl-cyclohexane, butyl-cyclopentane, butyl-cyclohexane, pentyl-cyclopentane, pentyl-cyclohexane, hexyl-cyclopentane, hexyl-cyclohexane, and isomers thereof.

Aryls will generally consist of an aromatic hydrocarbon in either an unsubstituted (phenyl), mono-substituted or multi-substituted form. In the case of mono-substituted and multi-substituted compounds, the substituted group may include a branched $C_{3+}$ alkyl, a straight chain $C_{1+}$ alkyl, a branched $C_{3+}$ alkylene, a straight chain $C_{2+}$ alkylene, a phenyl or a combination thereof. In one embodiment, at least one of the substituted groups include a branched $C_{3-12}$ alkyl, a straight chain $C_{1-12}$ alkyl, a branched $C_{3-12}$ alkylene, a straight chain $C_{2-12}$ alkylene, a phenyl or a combination thereof. In yet another embodiment, at least one of the substituted groups include a branched $C_{3-4}$ alkyl, a straight chain $C_{1-4}$ alkyl, a branched $C_{3-4}$ alkylene, straight chain $C_{2-4}$ alkylene, a phenyl or a combination thereof. Examples of various aryls include, without limitation, benzene, toluene, xylene (dimethylbenzene), ethyl benzene, para xylene, meta xylene, ortho xylene, $C_{9+}$ aromatics, butyl benzene, pentyl benzene, hexyl benzene, heptyl benzene, oxtyl benzene, nonyl benzene, decyl benzene, undecyl benzene, phenol, 4-ethyl phenol, 4-ethyl-2-methoxy phenol, 2-methoxy-4-propyl phenol, 4-propyl syringol, vanillin, and isomers thereof.

Fused aryls will generally consist of bicyclic and polycyclic aromatic hydrocarbons, in either an unsubstituted, mono-substituted, or multi-substituted form. In the case of mono-substituted and multi-substituted compounds, the substituted group may include a branched $C_{3+}$ alkyl, a straight chain $C_{1+}$ alkyl, a branched $C_{3+}$ alkylene, a straight chain $C_{2+}$ alkylene, a phenyl or a combination thereof. In another embodiment, at least one of the substituted groups include a branched $C_{3-4}$ alkyl, a straight chain $C_{1-4}$ alkyl, a branched $C_{3-4}$ alkylene, straight chain $C_{2-4}$ alkylene, a phenyl or a combination thereof. Examples of various fused aryls include, without limitation, naphthalene, anthracene, tetrahydronaphthalene, and decahydronaphthalene, indane, indene, and isomers thereof.

The $C_{4+}$ alcohols may also be cyclic, branched or straight chained, and have from 4 to 30 carbon atoms. In general, the $C_{4+}$ alcohols may be a compound according to the formula $R^1$—OH, wherein $R^1$ is a member selected from the group consisting of a branched $C_{4+}$ alkyl, straight chain $C_{4+}$ alkyl, a branched $C_{4+}$ alkylene, a straight chain $C_{4+}$ alkylene, a substituted $C_{5+}$ cycloalkane, an unsubstituted $C_{5+}$ cycloalkane, a substituted $C_{5+}$ cycloalkene, an unsubstituted $C_{5+}$ cycloalkene, an aryl, a phenyl and combinations thereof. Examples of desirable $C_{4+}$ alcohols include, without limitation, butanol, pentanol, hexanol, heptanol, octanol, nonanol, decanol, undecanol, dodecanol, tridecanol, tetradecanol, pentadecanol, hexadecanol, heptyldecanol, octyldecanol, nonyldecanol, eicosanol, uneicosanol, doeicosanol, trieicosanol, tetraeicosanol, and isomers thereof.

The $C_{4+}$ ketones may also be cyclic, branched or straight chained, and have from 4 to 30 carbon atoms. In general, the $C_{4+}$ ketone may be a compound according to the formula

wherein $R^3$ and $R^4$ are independently a member selected from the group consisting of a branched $C_{3+}$ alkyl, a straight chain $C_{1+}$ alkyl, a branched $C_{3+}$ alkylene, a straight chain $C_{2+}$ alkylene, a substituted $C_{5+}$ cycloalkane, an unsubstituted $C_{5+}$ cycloalkane, a substituted $C_{5+}$ cycloalkene, an unsubstituted $C_{5+}$ cycloalkene, an aryl, a phenyl and a combination thereof. Examples of desirable $C_{4+}$ ketones include, without limitation, butanone, pentanone, hexanone, heptanone, octanone, nonanone, decanone, undecanone, dodecanone, tridecanone, tetradecanone, pentadecanone, hexadecanone, heptyldecanone, octyldecanone, nonyldecanone, eicosanone, uneicosanone, doeicosanone, trieicosanone, tetraeicosanone, and isomers thereof.

The lighter fractions of the above, primarily $C_4$-$C_{12}$, may be separated for gasoline use. Moderate fractions, such as $C_7$-$C_{16}$, may be separated for jet fuel, while heavier fractions, i.e., $C_{11}$-$C_{24}$, may be separated for diesel use. The heaviest fractions may be used as lubricants or cracked to produce additional gasoline and/or diesel fractions. The $C_{4+}$ compounds may also find use as industrial chemicals, whether as an intermediate or an end product. For example, the aryls toluene, xylene, ethyl benzene, para xylene, meta xylene, ortho xylene may find use a chemical intermediates for the product of plastics and other products. Meanwhile, the $C_{9+}$ aromatics and fused aryls, such as naphthalene, anthracene, tetrahydronaphthalene, and decahydronaphthalene, may find use as solvents in industrial processes.

The following examples are included solely to provide a more complete disclosure of the subject invention. Thus, the following examples serve to illuminate the nature of the invention, but do not limit the scope of the invention disclosed and claimed herein in any fashion.

EXAMPLES

Example 1

A monometallic catalyst containing 5 wt % palladium on tungstated zirconia was prepared using incipient wetness techniques. An aqueous solution with a volume equal to the incipient wetness volume for the tungstated zirconia to be impregnated, 5.5 mL, and containing 1.3 g of palladium (II) nitrate hydrate (Alfa Aesar) was poured over 10 g tungstated zirconia (Norpro) and was shaken vigorously for 2 minutes. The catalyst was dried at 120° C. under vacuum for 3 hours. The catalyst was then calcined with air at a gradient temperature reaching 400° C. over a period of 4 hours. Once the desired temperature was reached, the catalyst was further soaked in air for an additional 6 hours.

Example 2

A monometallic catalyst containing 5 wt % palladium on monoclinic zirconia was prepared using incipient wetness techniques. An aqueous solution with a volume equal to the incipient wetness volume for the monoclinic zirconia to be impregnated, 3.3 mL, and containing 0.64 g of palladium (II) nitrate hydrate (Alfa Aesar) was applied dropwise to 5 g monoclinic zirconia (Norpro). The catalyst was dried at 120° C. under vacuum for 2 hours. The catalyst was then calcined with air at a gradient temperature reaching 400° C. over a period of 4 hours. Once the desired temperature was reached, the catalyst was further soaked in air for an additional 6 hours.

Example 3

A monometallic catalyst containing 5 wt % palladium supported on tetragonal zirconia was prepared using incipient wetness techniques. An aqueous solution with a volume equal to the incipient wetness volume for the tetragonal zirconia to be impregnated, 3.5 mL, and containing 0.56 g of palladium (II) nitrate hydrate (Alfa Aesar) was applied dropwise to 4.5 g tetragonal zirconia (Norpro). The catalyst was dried at 130° C. under vacuum for 3 hours. The catalyst was then calcined with air at a gradient temperature reaching 400° C. over a period of 4 hours. Once the desired temperature was reached, the catalyst was further soaked in air for an additional 6 hours.

Example 4

A monometallic catalyst containing 5 wt % palladium on rutile titania was prepared using incipient wetness techniques. An aqueous solution with a volume equal to the incipient wetness volume for the rutile titania to be impregnated, 2.7 mL, and containing 0.63 g of palladium (II) nitrate hydrate (Alfa Aesar) was applied dropwise to 5 g rutile titania (Alfa Aesar). The catalyst was dried at 140° C. under vacuum for 2 hours. The catalyst was then calcined with air at a gradient temperature reaching 400° C. over a period of 4 hours. Once the desired temperature was reached, the catalyst was further soaked in air for an additional 6 hours.

Example 5

A monometallic catalyst containing 5 wt % palladium on tungsten oxide was prepared using incipient wetness techniques. An aqueous solution with a volume equal to the incipient wetness volume for the tungsten oxide to be impregnated, 3.0 mL, and containing 0.56 g of palladium (II) nitrate hydrate (Alfa Aesar) was applied dropwise to 4.5 g tungsten oxide (Alfa Aesar). The catalyst was dried at 120° C. under vacuum for 3 hours. The catalyst was then calcined with air at a gradient temperature reaching 400° C. over a period of 4 hours. Once the desired temperature was reached, the catalyst was further soaked in air for an additional 6 hours.

Example 6

A monometallic catalyst containing 5 wt % palladium on niobia phosphate was prepared using incipient wetness techniques. An aqueous solution with a volume equal to the incipient wetness volume for the niobia phosphate to be impregnated, 7.5 mL, and containing 0.72 g of palladium (II) nitrate hydrate (Alfa Aesar) was applied dropwise to 5.76 g niobia phosphate. The catalyst was dried at 120° C. under vacuum for 3 hours. The catalyst was then calcined with air at a gradient temperature reaching 400° C. over a period of 4 hours. Once the desired temperature was reached, the catalyst was further soaked in air for an additional 6 hours.

Example 7

The catalysts defined in Examples 1-6 were tested to determine the impact of catalyst support for the conversion of a 50 wt % glycerol feedstock solution to monooxygenates, specifically alcohols and ketones. Before feed was introduced, each of the catalysts were reduced using hydrogen at a space velocity of 700 $hr^{-1}$, a 2 hour temperature gradient to 350° C., followed by a 2 hour hydrogen soak. The reactor system employed was a shell-in-tube reactor system as described in U.S. Pat. No. 7,767,867 to Cortright et al., which is incorporated herein by reference. The conditions were set at 270-290° C., 1050 psig, and a weight hour space velocity (WHSV) of 5 grams of glycerol per gram of catalyst per hour. The hydrogen was provided at an $H_2$/glycerol molar ratio of 4.

Table 1 includes the ten most abundant components produced. Relative catalyst reactivity varies between the different catalysts—as can be seen by the different temperature required to obtain measurable glycerol conversion. For each catalyst, a wide range of alcohols, ketones, and cyclic ethers were produced with monooxygenate yields (defined below) of 2-66%.

$$\text{Monooxygenate Yield} = \frac{\text{g Monooxygenate in Product}}{\text{g Feedstock Substrate (ie Glycerol etc)}}$$

$$\text{Glycerol Conversion} = 1 - \frac{\text{g Glycerol in Product}}{\text{g Feedstock Substrate (ie Glycerol etc)}}$$

TABLE 1

Hydrodeoxygenation product breakdown for palladium on various catalyst supports. Concentrations are represented as a weight percentage of the total carbon entering the system.

|  | 5% Pd on W—$ZrO_2$ | 5% Pd on $mZrO_2$ | 5% Pd on $tZrO_2$ | 5% Pd on $TiO_2$ | 5% Pd on $WO_3$ | 5% Pd on $NbPO_4$ |
|---|---|---|---|---|---|---|
| Temperature (° C.) | 270 | 290 | 290 | 290 | 290 | 290 |
| Propylene Glycol | 1.01% | 8.25% | 4.45% | 13.63% | 0.67% | 0.02% |
| Ethylene Glycol | 0.33% | 1.83% | 1.20% | 0.78% | 0.19% | 0.01% |
| Hydroxyacetone | 2.61% | 0.00% | 1.47% | 0.00% | 1.12% | 01.0% |
| Propionic Acid | 0.28% | 0.17% | 0.29% | 0.13% | 0.06% | 1.44% |
| Ethanol | 1.18% | 3.62% | 2.28% | 0.94% | 0.14% | 0.50% |
| 1-Propanol | 10.51% | 3.97% | 1.95% | 1.64% | 1.32% | 15.19% |
| Acetone | 0.01% | 0.59% | 0.31% | 1.36% | 0.05% | 0.28% |
| Ethane | 0.91% | 0.45% | 0.20% | 0.42% | 0.20% | 7.12% |
| Propane | 0.99% | 0.20% | 0.16% | 0.88% | 0.22% | 2.23% |
| Carbon Dioxide | 0.17% | 1.34% | 0.43% | 0.17% | 0.05% | 0.07% |
| Glycerol Conversion | 68.60% | 52.30% | 23.48% | 40.70% | 9.51% | 99.88% |
| Total Ketones and Aldehydes | 0.06% | 0.66% | 0.60% | 1.47% | 0.88% | 48.03% |
| Total Alcohols | 11.77% | 7.84% | 4.61% | 2.85% | 1.54% | 17.46% |
| Total Alkanes | 2.28% | 1.27% | 0.69% | 1.67% | 0.46% | 11.97% |
| Monooxygenate Yield | 11.83% | 9.06% | 5.22% | 5.61% | 2.42% | 66.51% |

Table 2 shows the carbon chain length for the products of the hydrodeoxygenation reaction of glycerol over a palladium catalyst on various supports. The inclusion of tungsten or phosphate within the support (W—$ZrO_2$ and $NbPO_4$) significantly increases the production of condensation products containing a carbon backbone of four or more as well as the unidentified aqueous product, which was identified by mass spectrometry as partially deoxygenated glycerol condensation products. However, tungsten as a support alone shows very limited reactivity for the hydrodeoxygenation reaction.

TABLE 2

Carbon chain length distribution for the hydrodeoxygenation by palladium on various catalyst supports with a glycerol feedstock. Concentrations are represented as a weight percentage of the total carbon entering the system.

|  | 5% Pd on W—ZrO2 | 5% Pd on mZ$_r$O2 | 5% Pd on tZrO2 | 5% Pd on TiO$_2$ | 5% Pd on WO$_3$ | 5% Pd on NbPO$_4$ |
|---|---|---|---|---|---|---|
| Temperature (° C.) | 270 | 290 | 290 | 290 | 290 | 290 |
| CO and CO$_2$ | 1.99% | 5.58% | 3.21% | 3.25% | 0.60% | 5.45% |
| C$_1$ | 4.3% | 0.6% | 0.6% | 0.32% | 0.10% | 0.22% |
| C$_2$ | 20.1% | 6.0% | 3.7% | 2.19% | 0.54% | 7.74% |
| C$_3$* | 24.5% | 64.9% | 86.9% | 77.94% | 94.64% | 51.18% |
| C$_{4+}$ | 24.9% | 4.4% | 0.5% | 5.08% | 0.66% | 26.51% |
| Unidentified Aqueous | 43.43% | 19.00% | 6.82% | 12.76% | 4.45% | 6.46% |

*The C$_3$ fraction includes unreacted glycerol.

Example 8

A catalyst containing 5 wt % palladium on 5 wt % tungsten modified rutile titania was prepared using incipient wetness techniques. An aqueous solution with a volume equal to the incipient wetness volume for the rutile titania to be impregnated, 3 mL, and containing 0.34 g of ammonium metatungstate hydrate (Sigma Aldrich) was applied dropwise to 5 g rutile titania (Alfa Aesar). The catalyst was dried at 130° C. under vacuum for 3 hours. The catalyst was then calcined with air at a gradient temperature reaching 400° C. over a period of 4 hours. Once the desired temperature was reached, the catalyst was further soaked in air for an additional 6 hours. An aqueous solution with a volume equal to the incipient wetness volume for the tungsten modified rutile titania to be impregnated, 3.2 mL, and containing 0.63 g of palladium (II) nitrate hydrate (Alfa Aesar) was applied dropwise to 5 g tungsten modified rutile titania. The catalyst was dried at 140° C. under vacuum for 2 hours. The catalyst was then calcined with air at a gradient temperature reaching 400° C. over a period of 4 hours. Once the desired temperature was reached, the catalyst was further soaked in air for an additional 6 hours.

Example 9

A catalyst containing 5 wt % palladium on 13.5 wt % tungsten modified monoclinic zirconia was prepared using incipient wetness techniques. An aqueous solution with a volume equal to the incipient wetness volume for the monoclinic zirconia to be impregnated, 3.0 mL, and containing 0.47 g of ammonium metatungstate hydrate (Alfa Aesar) was applied dropwise to 5 g monoclinic zirconia (Norpro). The catalyst was dried at 120° C. under vacuum for 3 hours. A second addition of an aqueous solution with a volume equal to the incipient wetness volume for the monoclinic zirconia to be impregnated, 3.0 mL, and containing 0.47 g of ammonium metatungstate hydrate (Alfa Aesar) was applied dropwise to the catalyst. The catalyst was dried at 120° C. under vacuum for 3 hours. The catalyst was then calcined with air at a gradient temperature reaching 400° C. over a period of 4 hours. Once the desired temperature was reached, the catalyst was further soaked in air for an additional 6 hours. Following the calcination, an aqueous solution with a volume equal to the incipient wetness volume for the catalyst to be impregnated, 3.0 mL, and containing 0.69 g of palladium (II) nitrate hydrate (Alfa Aesar) was applied dropwise to the catalyst. The catalyst was dried at 120° C. under vacuum for 3 hours. The catalyst was then calcined with air at a gradient temperature reaching 400° C. over a period of 4 hours. Once the desired temperature was reached, the catalyst was further soaked in air for an additional 6 hours.

Example 10

A catalyst containing 5 wt % palladium on 13.5 wt % tungsten modified tetragonal zirconia was prepared using incipient wetness techniques. An aqueous solution with a volume equal to the incipient wetness volume for the tetragonal zirconia to be impregnated, 3.0 mL, and containing 0.47 g of ammonium metatungstate hydrate (Alfa Aesar) was applied dropwise to 5 g tetragonal zirconia (Norpro). The catalyst was dried at 120° C. under vacuum for 3 hours. A second addition of an aqueous solution with a volume equal to the incipient wetness volume for the tetragonal zirconia to be impregnated, 3.0 mL, and containing 0.47 g of ammonium metatungstate hydrate (Alfa Aesar) was applied dropwise to the catalyst. The catalyst was dried at 120° C. under vacuum for 3 hours. The catalyst was then calcined with air at a gradient temperature reaching 400° C. over a period of 4 hours. Once the desired temperature was reached, the catalyst was further soaked in air for an additional 6 hours. Following the calcination, an aqueous solution with a volume equal to the incipient wetness volume for the catalyst to be impregnated, 3.0 mL, and containing 0.71 g of palladium (II) nitrate hydrate (Alfa Aesar) was applied dropwise to the catalyst. The catalyst was dried at 120° C. under vacuum for 3 hours. The catalyst was then calcined with air at a gradient temperature reaching 400° C. over a period of 4 hours. Once the desired temperature was reached, the catalyst was further soaked in air for an additional 6 hours.

Example 11

A catalyst containing 5 wt % palladium on 5 wt % tungsten modified monoclinic zirconia was prepared using incipient wetness techniques. An aqueous solution with a volume equal to the incipient wetness volume for the monoclinic zirconia to be impregnated, 3.9 mL, and containing 0.41 g of ammonium metatungstate hydrate (Alfa Aesar) was applied dropwise to 6.00 g tetragonal zirconia (Norpro). The catalyst was dried at 120° C. under vacuum for 3 hours. The catalyst was then calcined with air at a gradient temperature reaching 400° C. over a period of 4 hours. Once the desired temperature was reached, the catalyst was further soaked in air for an additional 6 hours. Following the calcination, an aqueous solution with a volume equal to the incipient wetness volume for the catalyst to be impregnated, 3.9 mL, and containing 0.76 g of palladium (II) nitrate hydrate (Alfa Aesar) was applied dropwise to the catalyst. The catalyst was dried at 120° C. under vacuum for 3 hours. The catalyst was then calcined with air at a gradient temperature reaching 400° C. over a period of 4 hours. Once the desired temperature was reached, the catalyst was further soaked in air for an additional 6 hours.

Example 12

Modification of the supports with tungsten, defined in Examples 8-11, allows for increased catalyst activity. These catalysts were tested to determine their performance in converting a 50 wt % glycerol feedstock solution to monooxygenates, specifically alcohols and ketones. Before feed was introduced, each of the catalysts were reduced using hydrogen at a space velocity of 700 hr$^{-1}$, a 2 hour temperature gradient to 350° C., followed by a 2 hour hydrogen soak. The conditions were set at 270-290° C., 1050 psig, and a weight hour space velocity (WHSV) of 5 grams glycerol per gram of catalyst per hour. The hydrogen was provided at an H$_2$/glycerol molar ratio of 4.

Table 3 includes the ten most abundant components produced. Relative catalyst reactivity varies between the different catalysts—as can be seen by the different temperature required to obtain glycerol conversion greater than 50%. For each catalyst, a wide range of alcohols, ketones and cyclic ethers were produced with monooxygenate yields of 15-28%.

TABLE 3

Hydrodeoxygenation product breakdown for Pd on various tungsten modified supports. Concentrations are represented as a weight percentage of the total carbon entering the system.

|  | 5% Pd on (5% W)—TiO$_2$ | 5% Pd on (13.5% W)—mZrO$_2$ | 5% Pd on (13.5% W)—tZrO$_2$ | 5% Pd on (5% W)—mZrO$_2$ |
|---|---|---|---|---|
| Temperature (° C.) | 290 | 270 | 270 | 290 |
| Propylene Glycol | 3.72% | 0.93% | 0.42% | 2.92% |
| Hydroxyacetone | 0.00% | 0.97% | 1.19% | 0.14% |
| Propionic Acid | 0.83% | 0.81% | 0.93% | 0.69% |
| Ethanol | 0.79% | 1.83% | 2.37% | 3.54% |
| 1-Propanol | 4.82% | 14.89% | 18.41% | 7.81% |
| Acetone | 1.38% | 0.34% | 0.35% | 1.12% |
| Propanal | 0.00% | 5.65% | 6.01% | 2.20% |
| Ethane | 1.28% | 0.09% | 2.41% | 1.34% |
| Propane | 2.50% | 0.09% | 1.92% | 0.47% |
| Carbon Dioxide | 0.12% | 0.11% | 0.39% | 0.71% |
| Glycerol Conversion | 57.15% | 64.07% | 72.35% | 61.46% |
| Total Ketones and Aldehydes | 1.61% | 6.30% | 6.79% | 3.42% |
| Total Alcohols | 5.96% | 16.97% | 21.35% | 11.92% |
| Total Alkanes | 4.03% | 0.71% | 4.76% | 3.11% |
| Monooxygenate Yield | 16.39% | 23.27% | 28.15% | 15.43% |

Example 13

A monometallic catalyst containing 2 wt % palladium on tungstated zirconia was prepared using incipient wetness techniques. An aqueous solution with a volume equal to the incipient wetness volume for the tungstated zirconia to be impregnated, 2.9 mL, and containing 0.24 g of palladium (II) nitrate hydrate (Alfa Aesar) was applied dropwise to 5.0 g tungstated zirconia (Norpro). The catalyst was dried at 120° C. under vacuum for 3 hours. The catalyst was then calcined with air at a gradient temperature reaching 400° C. over a period of 4 hours. Once the desired temperature was reached, the catalyst was further soaked in air for an additional 6 hours.

Example 14

A monometallic catalyst containing 2 wt % platinum on tungstated zirconia was prepared using incipient wetness techniques. An aqueous solution with a volume equal to the incipient wetness volume for the tungstated zirconia to be impregnated, 7.6 mL, and containing 0.51 g of dihydrogen hexachloroplatinate (IV) hexahydrate (Alfa Aesar) was applied dropwise to 10.0 g tungstated zirconia (Norpro). The catalyst was dried at 120° C. under vacuum for 3 hours. The catalyst was then calcined with air at a gradient temperature reaching 400° C. over a period of 4 hours. Once the desired temperature was reached, the catalyst was further soaked in air for an additional 6 hours.

Example 15

A monometallic catalyst containing 2 wt % nickel on tungstated zirconia was prepared using incipient wetness techniques. An aqueous solution with a volume equal to the incipient wetness volume for the tungstated zirconia to be impregnated, 6.8 mL, and containing 1.2 g of nickel (II) nitrate hexahydrate (Alfa Aesar) was applied dropwise to 12.0 g tungstated zirconia (Norpro). The catalyst was dried at 130° C. under vacuum for 2 hours. The catalyst was then calcined with air at a gradient temperature reaching 400° C. over a period of 4 hours. Once the desired temperature was reached, the catalyst was further soaked in air for an additional 6 hours.

Example 16

The catalysts defined in Examples 13-15 were tested to determine their performance in converting a 50 wt % glycerol feedstock solution to monooxygenates, specifically alcohols and ketones. Before feed was introduced, each of the catalysts was reduced using hydrogen at a space velocity of 700 hr$^{-1}$, a 2 hour temperature gradient to 350° C., followed by a 2 hour hydrogen soak. The conditions were set at 250-290° C., 1050 psig, and a weight hour space velocity (WHSV) of 5 grams glycerol per gram of catalyst per hour. The hydrogen was provided at an H$_2$/glycerol molar ratio of 4.

Table 4 includes the ten most abundant components produced. Relative catalyst reactivity varies between the different catalysts—as can be seen by the different temperature required to obtain glycerol conversion greater than 25%. For each catalyst, a wide range of alcohols, ketones, and cyclic ethers were produced with monooxygenate yields (defined above) of 10-44%.

TABLE 4

Hydrodeoxygenation product breakdown for Group VIII metal catalysts.
Concentrations are represented as a weight percentage
of the carbon entering the system.

|  | 2% Pd on W—ZrO$_2$ | 2% Ni on W—ZrO$_2$ | 2% Pt on W—ZrO$_2$ |
| --- | --- | --- | --- |
| Temperature (° C.) | 270 | 290 | 250 |
| Propylene Glycol | 0.47% | 1.80% | 3.58% |
| Ethylene Glycol | 0.15% | 0.16% | 0.22% |
| Hydroxyacetone | 1.86% | 3.88% | 0.87% |
| Propanoic Acid | 0.48% | 0.37% | 1.02% |
| Ethanol | 0.10% | 0.41% | 2.43% |
| 1-Propanol | 9.05% | 11.60% | 36.78% |
| Acetone | 0.18% | 0.36% | 3.26% |
| Propanal | 0.14% | 0.00% | 1.81% |
| Ethane | 0.66% | 0.14% | 4.81% |
| Carbon Dioxide | 0.05% | 0.06% | 4.94% |
| Glycerol Conversion | 43.14% | 26.10% | 99.87% |
| Total Ketones and Aldehydes | 0.30% | 0.58% | 5.19% |
| Total Alcohols | 10.14% | 13.73% | 40.14% |
| Total Alkanes | 1.37% | 0.24% | 18.28% |
| Monooxygenate Yield | 10.44% | 25.85% | 45.36% |

Table 5 shows the carbon chain length for the products for the hydrodeoxygenation reaction of glycerol over the Group VIII metal catalysts described in examples 13-15. Platinum shows the greatest amount of carbon scission reactions (through the production of components with less than 3 carbons) and nickel shows the greatest amount of condensation products (through the production of components containing a carbon backbone of four or more as well as the unidentified aqueous product). Mass spectrometry identification indicates that the unidentified aqueous product is partially deoxygenated glycerol condensation products.

TABLE 5

Carbon number distribution for the hydrodeoxygenation product profile
of Group VIII metal catalysts. Concentrations are represented as a
weight percentage of the total carbon entering the system.

|  | 2% Pd on W—ZrO$_2$ | 2% Ni on W—ZrO$_2$ | 2% Pt on W—ZrO$_2$ |
| --- | --- | --- | --- |
| Temperature (° C.) | 270 | 290 | 250 |
| CO and CO$_2$ | 1.24% | 0.36% | 5.15% |
| C$_1$ | 0.24% | 0.21% | 0.50% |
| C$_2$ | 1.63% | 0.77% | 7.68% |
| C$_3$* | 54.58% | 46.71% | 70.02% |
| C$_{4+}$ | 11.00% | 16.63% | 1.74% |
| Unidentified Aqueous | 30.14% | 34.72% | 8.98% |

*The C$_3$ fraction includes unreacted glycerol.

Example 17

A bimetallic catalyst containing 2 wt % palladium and 2 wt % molybdenum, supported on tungstated zirconia, was prepared using incipient wetness techniques. An aqueous solution with a volume equal to the incipient wetness volume for the tungstated zirconia to be impregnated, 2.9 mL, and containing 0.24 g of palladium (II) nitrate hydrate (Alfa Aesar) and 0.17 g of ammonium molybdate (VI) tetrahydrate (Sigma Aldrich) was applied dropwise to 5.1 g tungstated zirconia (Norpro). The catalyst was dried at 130° C. under vacuum for 2 hours. The catalyst was then calcined with air at a gradient temperature reaching 400° C. over a period of 4 hours. Once the desired temperature was reached, the catalyst was further soaked in air for an additional 6 hours.

Example 18

A bimetallic catalyst containing 2 wt % platinum and 5 wt % molybdenum, supported on tungstated zirconia, was prepared using incipient wetness techniques. An aqueous solution with a volume equal to the incipient wetness volume for the tungstated zirconia to be impregnated, 3.3 mL, and containing 0.46 g of ammonium molybdate (VI) tetrahydrate (Sigma Aldrich) was applied dropwise to 5.0 g tungstated zirconia (Norpro). The catalyst was dried at 130° C. under vacuum for 14 hours. An aqueous solution with a volume equal to the incipient wetness volume for the tungstated zirconia to be impregnated, 3.3 mL, and containing 0.25 g of dihydrogen hexachloroplatinate (IV) hexahydrate (Alfa Aesar) was applied dropwise to the catalyst. The catalyst was dried at 130° C. under vacuum for 3 hours. The catalyst was then calcined with air at a gradient temperature reaching 400° C. over a period of 4 hours. Once the desired temperature was reached, the catalyst was further soaked in air for an additional 6 hours.

Example 19

A bimetallic catalyst containing 8 wt % nickel and 4 wt % molybdenum, supported on tungstated zirconia, was prepared using incipient wetness techniques. An aqueous solution with a volume equal to the incipient wetness volume for the tungstated zirconia to be impregnated, 4.6 mL, and containing 3.2 g of nickel (II) nitrate hexahydrate (Alfa Aesar) and 0.59 g of ammonium molybdate (VI) tetrahydrate (Sigma Aldrich) was applied dropwise to 8.0 g tungstated zirconia (Norpro). The catalyst was dried at 120° C. under vacuum for 14 hours. The catalyst was then calcined with air at a gradient temperature reaching 400° C. over a period of 4 hours. Once the desired temperature was reached, the catalyst was further soaked in air for an additional 6 hours.

Example 20

A bimetallic catalyst containing 2 wt % palladium and 0.5 wt % tin supported, on tungstated zirconia, was prepared using incipient wetness techniques. An aqueous solution with a volume equal to the incipient wetness volume for the tungstated zirconia to be impregnated, 2.5 mL, and containing 0.25 g of palladium (II) nitrate hydrate (Alfa Aesar) and 0.08 g of tin (IV) chloride pentahydrate (Riedel de Haen) was applied dropwise to 5.0 g tungstated zirconia (Norpro). The catalyst was dried at 120° C. under vacuum for 2 hours. The catalyst was then calcined with air at a gradient temperature reaching 400° C. over a period of 4 hours. Once the desired temperature was reached, the catalyst was further soaked in air for an additional 6 hours.

Example 21

A bimetallic catalyst containing 4 wt % nickel and 0.65 wt % tin, supported on tungstated zirconia, was prepared using incipient wetness techniques. An aqueous solution with a volume equal to the incipient wetness volume for the tungstated zirconia to be impregnated, 3.0 mL, and containing 0.99 g of nickel (II) nitrate hexahydrate (Alfa Aesar) and 0.10 g of tin (IV) chloride pentahydrate (Riedel de Haen) was applied dropwise to 5.0 g tungstated zirconia (Norpro). The catalyst was dried at 120° C. under vacuum for 2 hours. The catalyst was then calcined with air at a gradient temperature reaching 400° C. over a period of 4 hours. Once the desired temperature was reached, the catalyst was further soaked in air for an additional 6 hours.

Example 22

A bimetallic catalyst containing 5 wt % palladium and 5 wt % rhenium, supported on tungstated zirconia, was prepared using incipient wetness techniques. An aqueous solution with a volume equal to the incipient wetness volume for the tungstated zirconia to be impregnated, 6.8 mL, and containing 1.5 g palladium (II) nitrate hydrate (Alfa Aesar) and 1.1 g perrhenic acid (Alfa Aesar) was applied dropwise to 12.1 g tungstated zirconia (Norpro). The catalyst was dried at 120° C. under vacuum for 2 hours. The catalyst was then calcined with air at a gradient temperature reaching 400° C. over a period of 4 hours. Once the desired temperature was reached, the catalyst was further soaked in air for an additional 6 hours.

Example 23

Modification of the Group VIII metals (nickel, palladium, and platinum) by molybdenum, rhenium or tin defined in Examples 17-22 allows for an increase in the amount of monooxygenates produced while limiting the production of undesirable alkanes and carbon dioxide. These catalysts were tested to determine their performance in converting a 50 wt % glycerol feedstock to monooxygenates, specifically alcohols and ketones. Before feed was introduced, each of the catalysts was reduced using hydrogen at a space velocity of 700 hr$^{-1}$, a 2 hour temperature gradient to 350° C., followed by a 2 hour hydrogen soak. The conditions were set at 250-290° C., 1050 psig, and a weight hour space velocity (WHSV) of 5 grams glycerol per gram of catalyst per hour. The hydrogen was provided at an $H_2$/glycerol molar ratio of 4.

Table 6 includes the ten most abundant components produced. Relative catalyst reactivity varies between the different catalysts—as can be seen by the different temperature required to obtain glycerol conversion of about 25% or greater. For each catalyst, a wide range of alcohols, ketones, and cyclic ethers were produced with monooxygenate yields of 7-63%.

Example 24

A trimetallic catalyst containing 2 wt % palladium, 2 wt % molybdenum, and 0.5 wt % tin, supported on tungstated zirconia, was prepared using incipient wetness techniques. An aqueous solution with a volume equal to the incipient wetness volume for the tungstated zirconia to be impregnated, 60 mL, and containing 2.2 g tin (IV) chloride pentahydrate (Riedel de Haen) was applied dropwise to 145 g tungstated zirconia (Norpro). The catalyst was dried at 120° C. under vacuum for 2 hours. The catalyst was then calcined with air at a gradient temperature reaching 400° C. over a period of 4 hours. Once the desired temperature was reached the catalyst was further soaked in air for an additional period of 6 hours. An aqueous solution with a volume equal to the incipient wetness volume for the tin/tungstated zirconia catalyst to be impregnated, 60 mL, and containing 5.4 g of ammonium molybdate (VI) tetrahydrate (Sigma Aldrich) was applied dropwise to the calcined catalyst. The catalyst was dried at 120° C. under vacuum for 2 hours. An aqueous solution with a volume equal to the incipient wetness volume for the catalyst to be impregnated, 50 mL, and containing 7.4 g palladium (II) nitrate hydrate (Alfa Aesar) was applied dropwise to the catalyst. The catalyst was dried at 120° C. under vacuum for 2 hours. The catalyst was then calcined with air at a gradient temperature reaching 400° C. over a period of 4 hours. Once the desired temperature was reached the catalyst was further soaked in air for an additional period of 6 hours.

Example 25

A trimetallic catalyst containing 4 wt % nickel, 2 wt % molybdenum, and 0.65 wt % tin, supported on tungstated zirconia, was prepared using incipient wetness techniques. An aqueous solution with a volume equal to the incipient wetness volume for the tungstated zirconia to be impregnated, 3 mL, and containing 0.09 g tin (IV) chloride pentahy-

TABLE 6

Hydrodeoxygenation product breakdown for Mo, Re or Sn modified Group VIII metal catalysts with a glycerol feedstock. Concentrations are represented as a weight percentage of the total carbon entering the system.

|  | 2% Pd 2% Mo on W—$ZrO_2$ | 2% Pt 5% Mo on W—$ZrO_2$ | 8% Ni 4% Mo on W—$ZrO_2$ | 2% Pd 0.5% Sn on W—$ZrO_2$ | 4% Ni 0.65% Sn on W—$ZrO_2$ | 5% Pd 5% Re on W—$ZrO_2$ |
|---|---|---|---|---|---|---|
| Temperature (° C.) | 270 | 270 | 290 | 250 | 270 | 250 |
| Propylene Glycol | 1.56% | 3.28% | 3.53% | 12.96% | 3.75% | 7.72% |
| Ethylene Glycol | 0.22% | 0.11% | 0.15% | 0.36% | 0.09% | 0.83% |
| Hydroxyacetone | 2.13% | 3.38% | 5.83% | 1.48% | 2.99% | 1.46% |
| Propanoic Acid | 1.15% | 0.81% | 0.42% | 0.48% | 0.26% | 1.07% |
| Ethanol | 1.47% | 0.18% | 0.08% | 0.83% | 0.10% | 4.23% |
| 1-Propanol | 23.15% | 13.15% | 4.71% | 18.06% | 5.86% | 55.51% |
| Acetone | 1.31% | 2.09% | 1.47% | 0.38% | 0.42% | 1.56% |
| Ethane | 0.54% | 0.18% | 0.04% | 0.07% | 0.09% | 0.27% |
| Propane | 2.66% | 1.40% | 0.00% | 0.80% | 0.20% | 2.11% |
| Carbon Dioxide | 0.31% | 0.16% | 0.05% | 0.32% | 0.04% | 0.94% |
| Glycerol Conversion | 80.44% | 59.60% | 62.29% | 46.99% | 24.63% | 92.08% |
| Total Ketones and Aldehydes | 9.52% | 2.32% | 1.53% | 1.66% | 0.51% | 1.80% |
| Total Alcohols | 25.51% | 13.90% | 4.95% | 19.27% | 6.18% | 61.06% |
| Total Alkanes | 3.53% | 1.58% | 0.30% | 0.91% | 0.29% | 2.79% |
| Monooxygenate Yield | 35.06% | 16.57% | 15.75% | 21.15% | 6.70% | 62.89% | drate (Riedel de Haen) was applied dropwise to 5 g tungstated zirconia (Norpro). The catalyst was dried at 120° C. under vacuum for 2 hours. An aqueous solution with a volume equal to the incipient wetness volume for the tin/tungstated zirconia catalyst to be impregnated, 3 mL, and containing 0.2 g of ammonium molybdate (VI) tetrahydrate (Sigma Aldrich) and containing 1.0 g nickel (II) nitrate hexahydrate (Alfa Aesar) was applied dropwise to the tin/tungstated zirconia catalyst. The catalyst was dried at 120° C. under vacuum for 2 hours. The catalyst was then calcined with air at a gradient temperature reaching 400° C. over a period of 4 hours. Once the desired temperature was reached the catalyst was further soaked in air for an additional period of 6 hours.

Example 26

A trimetallic catalyst containing 2 wt % platinum, 5 wt % molybdenum, and 1 wt % tin, supported on tungstated zirconia, was prepared using incipient wetness techniques. An aqueous solution with a volume equal to the incipient wetness volume for the tungstated zirconia to be impregnated, 40 mL, and containing 5.5 g of ammonium molybdate (VI) tetrahydrate (Sigma Aldrich) was applied dropwise to 60 g tungstated zirconia (Norpro). The catalyst was dried at 120° C. under vacuum for 2 hours. An aqueous solution with a volume equal to the incipient wetness volume for the molybdenum/tungstated zirconia catalyst to be impregnated, 3.2 mL, and containing 0.25 g of dihydrogen hexachloroplatinate (IV) hexahydrate (Alfa Aesar) and 0.01 g tin (II) chloride dehydrate (Alfa Aesar) was applied dropwise to 5 g of the molybdenum/tungstated zirconia catalyst. The catalyst was dried at 120° C. under vacuum for 2 hours. The catalyst was then calcined with air at a gradient temperature reaching 400° C. over a period of 4 hours. Once the desired temperature was reached the catalyst was further soaked in air for an additional period of 6 hours.

Example 27

Modifying palladium with molybdenum and tin as described in Example 24 shows an increase in the amount of monooxygenates produced while limiting the production of undesirable alkanes and carbon dioxide when compared to the platinum and nickel catalysts described in Examples 25 and 26. These catalysts were tested to determine their performance in converting a 50 wt % glycerol feedstock to monooxygenates, specifically alcohols and ketones. Before feed was introduced, each of the catalysts was reduced using hydrogen at a space velocity of 700 hr$^{-1}$, a 2 hour temperature gradient to 350° C., followed by a 2 hour hydrogen soak. The conditions were set at 250-290° C., 1050 psig, and a weight hour space velocity (WHSV) of 5 grams glycerol per gram of catalyst per hour. The hydrogen was provided at an H$_2$/glycerol molar ratio of 4.

Table 7 includes the ten most abundant components produced. Relative catalyst reactivity varies between the different catalysts—as can be seen by the different temperature required to obtain glycerol conversion greater than 75%. For each catalyst, a wide range of alcohols, ketones and cyclic ethers were produced with monooxygenate yields of 3-38%.

TABLE 7

Hydrodeoxygenation product breakdown for Mo and Sn modified Group VIII metal catalysts with a glycerol feedstock. Concentrations are represented as a weight percentage of the total carbon entering the system.

|  | 2% Pd 2% Mo 0.65% Sn on W—ZrO$_2$ | 4% Ni 2% Mo 0.65% Sn on W—ZrO$_2$ | 2% Pt 5% Mo 1% Sn on W—ZrO$_2$ |
|---|---|---|---|
| Temperature (° C.) | 270 | 290 | 270 |
| Propylene Glycol | 3.1% | 4.1% | 0.2% |
| Ethylene Glycol | 0.2% | 0.2% | 0.0% |
| Hydroxyacetone | 3.0% | 6.4% | 0.0% |
| Propanoic Acid | 3.5% | 1.5% | 1.7% |
| Ethanol | 2.0% | 0.3% | 0.4% |
| 1-Propanol | 18.6% | 13.6% | 2.3% |
| Acetone | 1.3% | 2.3% | 0.1% |
| Ethane | 0.1% | 0.2% | 7.3% |
| Propane | 1.2% | 0.9% | 46.2% |
| Carbon Dioxide | 1.6% | 0.1% | 6.3% |
| Glycerol Conversion | 85.4% | 83.5% | 98.9% |
| Total Ketones and Aldehydes | 10.4% | 2.9% | 0.1% |
| Total Alcohols | 24.3% | 15.8% | 2.8% |
| Total Alkanes | 3.7% | 1.1% | 77.3% |
| Monooxygenate Yield | 38.4% | 23.6% | 3.0% |

Example 28

Modifying palladium catalysts with Mo, Sn, and the combination of Mo and Sn described in Example 24 significantly improves the monooxygenate yield while limiting the amount of undesirable alkanes and carbon dioxide produced and preserving the carbon backbone of the feed. These catalysts were tested to determine their performance in converting a 50 wt % 43 dextrose equivalent (DE) food grade corn syrup feedstock to monooxygenates, specifically alcohols, ketones, and cyclic ethers. Before feed was introduced, each of the catalysts was reduced using hydrogen at a space velocity of 700 hr$^{-1}$, a 2 hour temperature gradient to 350° C., followed by a 2 hour hydrogen soak. The conditions were set with a temperature gradient through the reactor from 180-255° C., 1050 psig, and a weight hour space velocity (WHSV) of 0.5 grams corn syrup per gram of catalyst per hour. The hydrogen was provided at an H$_2$/carbon molar ratio of 2.

Table 8 includes a class breakdown of the components produced. Relative catalyst reactivity varies between the different catalysts—as can be seen by the residual polyoxygenates and unidentified aqueous product. Mass spectrometer quantification indicates that the unidentified aqueous is composed of partially deoxygenated sugar fragments. For each catalyst, a wide range of alcohols, ketones, and cyclic ethers were produced with monooxygenate yields of 34-55%.

TABLE 8

Hydrodeoxygenation product breakdown for modified palladium catalysts with a corn syrup feedstock. Concentrations are represented as a weight percentage of the total carbon entering the system.

|  | 3% Pd on W—ZrO$_2$ | 3% Pd 0.65% Sn on W—ZrO$_2$ | 2% Pd 2% Mo on W—ZrO$_2$ | 2% Pd 2% Mo 0.5% Sn on W—ZrO$_2$ |
|---|---|---|---|---|
| CO and CO$_2$ | 1.67% | 1.17% | 0.68% | 1.62% |
| Paraffins | 2.74% | 3.27% | 4.01% | 10.69% |

TABLE 8-continued

Hydrodeoxygenation product breakdown for modified palladium catalysts with a corn syrup feedstock. Concentrations are represented as a weight percentage of the total carbon entering the system.

|  | 3% Pd on W—$ZrO_2$ | 3% Pd 0.65% Sn on W—$ZrO_2$ | 2% Pd 2% Mo on W—$ZrO_2$ | 2% Pd 2% Mo 0.5% Sn on W—$ZrO_2$ |
| --- | --- | --- | --- | --- |
| Alcohols | 9.81% | 14.84% | 15.27% | 25.11% |
| Ketones and Aldehydes | 7.42% | 1.53% | 1.61% | 1.64% |
| Cyclic Ethers | 30.08% | 17.00% | 17.07% | 25.80% |
| Acids | 0.96% | 0.69% | 0.98% | 0.71% |
| Dioxygenates | 3.53% | 7.92% | 6.69% | 4.74% |
| Polyoxygenates | 1.67% | 6.14% | 9.43% | 1.99% |
| Unidentified Aqueous | 24.20% | 38.11% | 26.94% | 24.39% |
| Monooxygenate Yield | 55.62% | 34.05% | 34.93% | 53.26% |

Table 9 shows the carbon number distribution for the modified palladium catalysts. As corn syrup is a glucose oligomer, it is important to note that none of the $C_{7+}$ products are sugars, rather, the $C_{7+}$ products are condensation products of the hydrolyzed and deoxygenated glucose oligomers. The higher amount of condensation products produced with the 3 wt % palladium on tungsted zirconia catalyst has significant negative impact on system operability. Over time these condensation products tend to accumulate resulting in a pressure drop across the reactor that may require a system shut down and/or catalyst regeneration.

TABLE 9

Carbon number distribution for the hydrodeoxygenation of corn syrup with modified palladium catalysts. Concentrations are represented as a weight percentage of the total carbon entering the system.

|  | 3% Pd on W—$ZrO_2$ | 3% Pd 0.65% Sn on W—$ZrO_2$ | 2% Pd 2% Mo on W—$ZrO_2$ | 2% Pd 2% Mo 0.5% Sn on W—$ZrO_2$ |
| --- | --- | --- | --- | --- |
| CO + $CO_2$ | 1.67% | 1.17% | 0.68% | 1.62% |
| $C_1$ | 0.40% | 0.54% | 0.18% | 0.04% |
| $C_2$ | 1.13% | 2.29% | 1.62% | 2.46% |
| $C_3$ | 2.43% | 10.47% | 7.31% | 8.23% |
| $C_4$ | 0.85% | 3.26% | 4.24% | 3.37% |
| $C_5$ | 4.89% | 5.94% | 5.50% | 8.77% |
| $C_6$ | 40.89% | 29.71% | 39.55% | 48.53% |
| $C_{7+}$ | 16.55% | 3.06% | 4.58% | 3.99% |
| Unidentified Aqueous | 24.20% | 38.11% | 26.94% | 24.39% |

Examples 29, 30, 31 and 32 were conducted using the apparatus illustrated in FIG. 1B—a reactive system including an aqueous recycle stream. Hydrodeoxygenation (HDO) catalysts prepared according to Example 24 were evaluated for converting a 60 wt % 43 DE food grade corn syrup feedstock. The impact of operating pressure and regeneration methods on product and carbon number distribution were examined, with the results shown in Table 10 and Table 11, respectively.

Example 29

Prior to operation the catalyst from Example 24 was reduced under atmospheric pressure using hydrogen at a gas hourly space velocity of 450 $hr^{-1}$, with a 3 hour temperature ramp to 400° C., followed by a 3 hour temperature soak while $H_2$ was still flowing. The reaction conditions were set with a temperature gradient through the reactor from 150-264° C., 1050 psig, and a weight hour space velocity (WHSV) of 0.8 grams corn syrup per gram of catalyst per hour. Hydrogen was provided at an $H_2$/carbon molar ratio of 1.6. The mass ratio of aqueous recycle to fresh feed was 3.6.

Example 30

The catalyst from Example 29 was subjected to an oxidative regeneration in order to remove carbonaceous deposits that formed on the catalyst. The catalyst was purged with $N_2$ at 50 psig until no hydrocarbons were detected in the gas by means of gas chromatography flame ionization detector (GC-FID). Then a mixture of 1% $O_2$ (by mixing $N_2$ and air) was fed to the reactor at a GHSV of 2400 $hr^{-1}$. The reactor off-gas composition was analyzed by IR spectroscopy to detect CO and $CO_2$. The temperature was increased from 350° C. to 405° C. in 3 hours, then increased to 445° C. in 3 hours, then increased to 470° C. in 2.5 hours, then held at 470° C. until $CO_2$ levels in the off-gas had decreased to 1000 ppm. Then the ratio of $N_2$ and air that was being fed to the reactor was changed to achieve a concentration of 5% $O_2$. This gas mixture was fed to the reactor at 470° C. until the $CO_2$ level in the off-gas decreased to 1000 ppm. Then the air supply to the reactor was stopped and the reactor was cooled down to the operating temperatures of Example 29 while $N_2$ was still flowing. The $N_2$ was then stopped and the $H_2$ co-feed was then resumed at the same rate as Example 29 and the reactor was pressurized to 1050 psig. Then DI water was fed to the reactor until the system was inventoried with liquid and the desired aqueous recycle flow rate of Example 29 was achieved. Then the feed was switched to 60% 43DE corn syrup. At this point the catalyst was subjected to the same experimental conditions of Example 29.

Example 31

A catalyst prepared in the same manner as Example 24 was evaluated at the same conditions as Example 29 except that the temperature gradient through the reactor ranged from 168-276° C., and the operating pressure was increased from 1050 psig to 1800 psig.

Example 32

The catalyst of Example 31 was regenerated with $H_2$ in order to remove carbonaceous deposits. The catalyst was purged with water and $H_2$ at 1800 psig and the temperature of the reactor was decreased to 200° C. Then, the water was stopped and $H_2$ was fed to the reactor at a GHSV of 600 $hr^{-1}$ to remove water from the catalyst bed. The temperature was increased from 200° C. to 400° C. over 6 hours while continuing to flow $H_2$, then held at 400° C. until the levels of alkanes in the off-gas had decreased to below 1000 ppm. Then the reactor was cooled down to the operating temperatures of Example 31 while $H_2$ was still flowing. The experimental conditions of Example 31 were then repeated.

Table 10 includes a class breakdown of the components produced and Table 11 shows the carbon number distribution for the modified palladium catalysts under various operating conditions (e.g., pressure and regeneration).

TABLE 10

Hydrodeoxygenation product breakdown for modified palladium catalysts with a corn syrup feedstock. Concentrations are represented as a carbon weight percentage of the total carbon entering the system.

| | Example | | | |
|---|---|---|---|---|
| | 29 | 30 | 31 | 32 |
| Pressure | 1050 psig | 1050 psig | 1800 psig | 1800 psig |
| Catalyst Regeneration | None | Oxidation | None | High Pressure Hydrogen |
| CO and $CO_2$ | 3.3% | 1.5% | 0.9% | 0.9% |
| Alkanes | 5.9% | 4.1% | 7.9% | 8.8% |
| Alcohols | 22.7% | 20.2% | 22.1% | 21.8% |
| Ketones and Aldehydes | 4.8% | 9.1% | 0.9% | 1.2% |
| Cyclic Ethers | 20.4% | 17.0% | 21.4% | 21.6% |
| Cyclic Ketones | 2.2% | 6.3% | 0.8% | 0.8% |
| Diols | 8.5% | 6.4% | 5.6% | 6.8% |
| Acids | 3.8% | 3.7% | 2.0% | 1.4% |
| Other Di-oxygenates | 1.2% | 1.9% | 0.5% | 0.3% |
| Polyoxygenates | 3.0% | 3.3% | 5.2% | 5.6% |
| Unidentified Aqueous | 22.8% | 19.2% | 30.9% | 32.2% |
| Monooxygenate Yield | 50.1% | 52.6% | 45.2% | 45.4% |
| pH of Aqueous Phase | 2.71 | 2.76 | 3.24 | 3.06 |

TABLE 11

Carbon number distribution for the hydrodeoxygenation of corn syrup with modified palladium catalysts. Concentrations are represented as a carbon weight percentage of the total carbon entering the system.

| | Example | | | |
|---|---|---|---|---|
| | 29 | 30 | 31 | 32 |
| $C_1$ | 0.4% | 0.4% | 0.1% | 0.3% |
| $C_2$ | 3.8% | 2.5% | 2.7% | 3.0% |
| $C_3$ | 12.0% | 10.4% | 8.0% | 9.8% |
| $C_4$ | 5.5% | 5.2% | 4.0% | 4.6% |
| $C_5$ | 8.5% | 7.2% | 7.4% | 7.0% |
| $C_6$ | 41.0% | 43.2% | 42.9% | 42.2% |
| $C_{7+}$ | 5.0% | 7.9% | 2.3% | 2.4% |

The results indicate that the operating conditions can be used to impact the HDO catalyst selectivity. At lower pressure, more ketones, acids, and condensation products are produced compared to operating at higher pressure. Regeneration can also be used to modify the catalyst selectivity. An increase in ketones, acids, and condensation products was achieved via oxidative regeneration. While regeneration with hydrogen shifted the product selectivity away from ketones, acids, and long chain components. Depending on the desired final product, either type of selectivity may be desirable. Further hydrogenation and hydrotreating of the $C_{7+}$ condensed components leads directly to long chain alkanes, isoalkanes, and naphthenes suitable for incorporating into gasoline, jet, and diesel fuels.

Example 33

The previously described HDO catalysts can be incorporated into a system for the production of liquid fuels and chemicals as described in International Patent No. WO 2008/109877 to Cortright et al., which is incorporated herein by reference.

FIG. 2 is a representative flow scheme that may be utilized for the production of chemicals and gasoline from biomass-derived feedstocks. The hydrodeoxygenation reactor is connected to an acid condensation reactor and utilizes various recycle streams to maximize product yields and manage rates of catalyst deactivation.

The HDO reactor contained the catalyst described in Example 24 and the acid condensation (AC) reactor utilized a nickel modified ZSM-5 catalyst. These catalysts were tested to determine their performance in converting a 60 wt % sucrose feedstock to gasoline and chemicals. Before feed was introduced, the HDO catalyst was reduced using hydrogen at a space velocity of 700 hr$^{-1}$, a 3 hour temperature gradient to 350° C., followed by a 3 hour hydrogen soak; the AC catalyst was heated under flowing nitrogen to 350° C. The HDO reactor had a temperature gradient from 170-300° C., 1800 psig, and a weight hour space velocity (WHSV) of 0.5 grams sucrose per gram of catalyst per hour. The hydrogen was provided at an $H_2$/carbon molar ratio of 2.5 and the aqueous recycle was set to a 4:1 recycle to fresh feed weight ratio. The AC reactor was set to a temperature of 350° C., 450 psig, and a weight hour space velocity (WHSV) of approximately 0.5 grams sucrose per gram catalyst per hour. The light hydrocarbon recycle was set to a 0.15:1 recycle to acid condensation feed weight ratio and the vapor recycle was set to a 0.75 recycle to acid condensation feed weight ratio. The distillation column was set up to produce a product stream with an initial boiling point of approximately 50° C. at an operating pressure of 350 psig.

Figure 3:
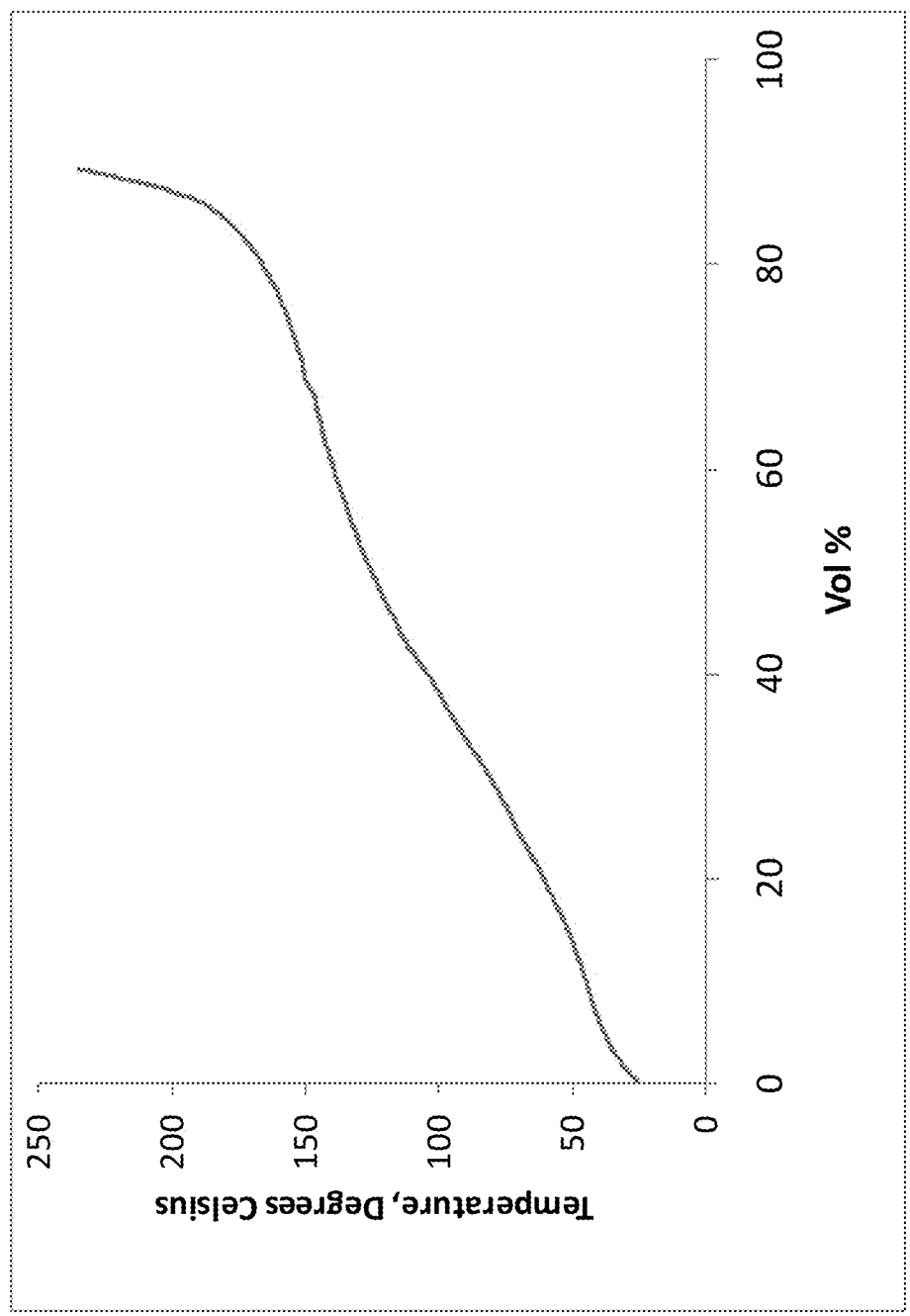
FIG. 3 is a chart illustrating the boiling point curve of the products produced in a hydrodeoxygenation (HDO) and acid condensation (AC) reactor system according to the present invention.
Figure 4:
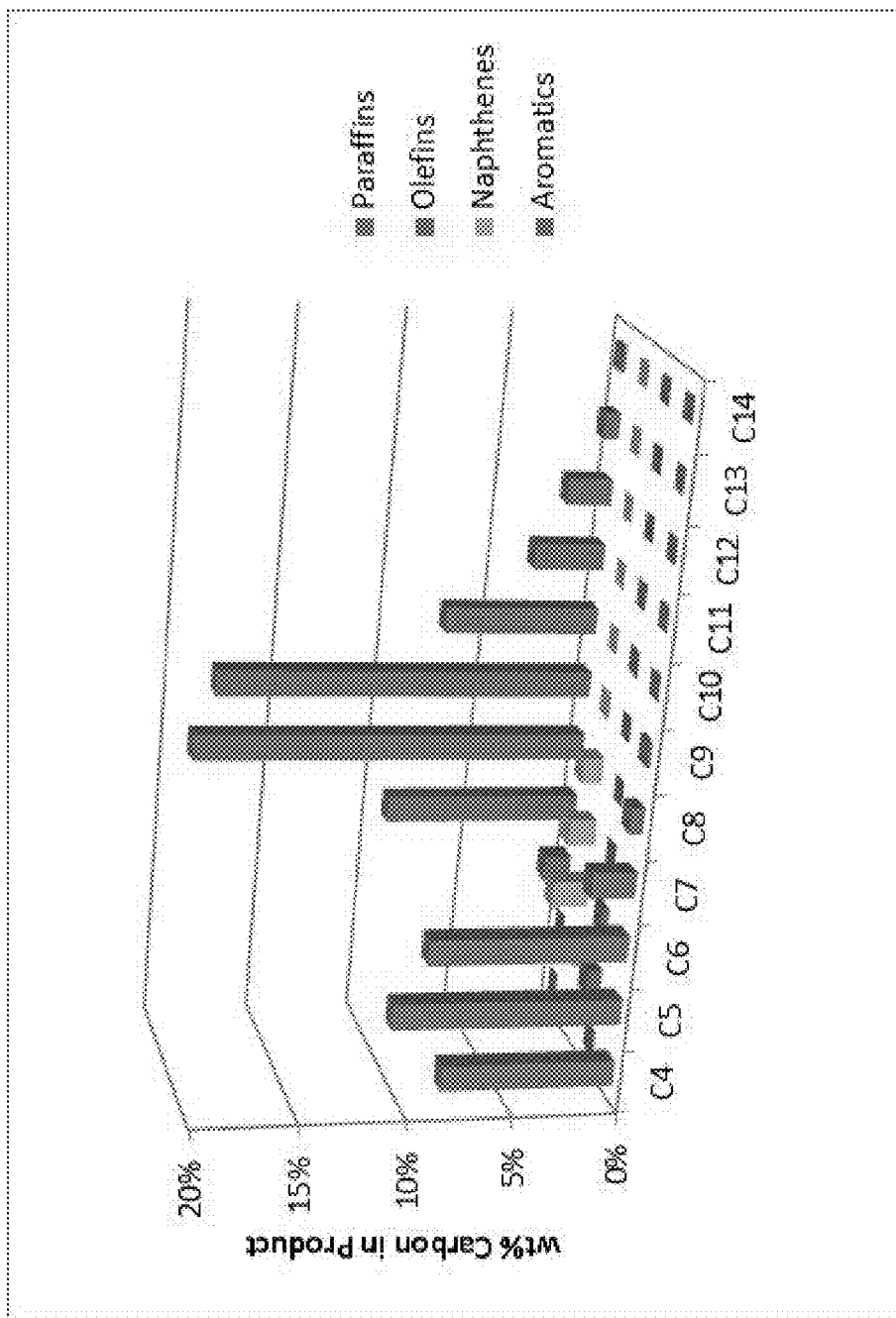
FIG. 4 is a chart illustrating the product distribution yields resulting from using the HDO-AC reactor system.

FIG. 3 shows a boiling point curve for the final product of the 2 wt % palladium, 2 wt % molybdenum, 0.5 wt % tin (HDO) and nickel modified ZSM-5 (AC) reactor system. With a final fractionation to remove the residual heavy products, the HDO-AC product could be classified as a finished reformate and gasoline blendstock. The highly aromatic product profile of the HDO-AC reactor system provides a unique opportunity to capitalize on the benzene, toluene and xylene fractions present in the product profile shown in FIG. 4.

Example 34

A trimetallic catalyst containing 2 wt % palladium, 2 wt % molybdenum, and 0.5 wt % tin, supported on tungstated zirconia, was prepared using the methods described above. The catalyst was tested to determine its performance in converting lignin model compounds, guaiacol and ferulic acid, to lower molecular weight oxygenated compounds.

Figure 5:
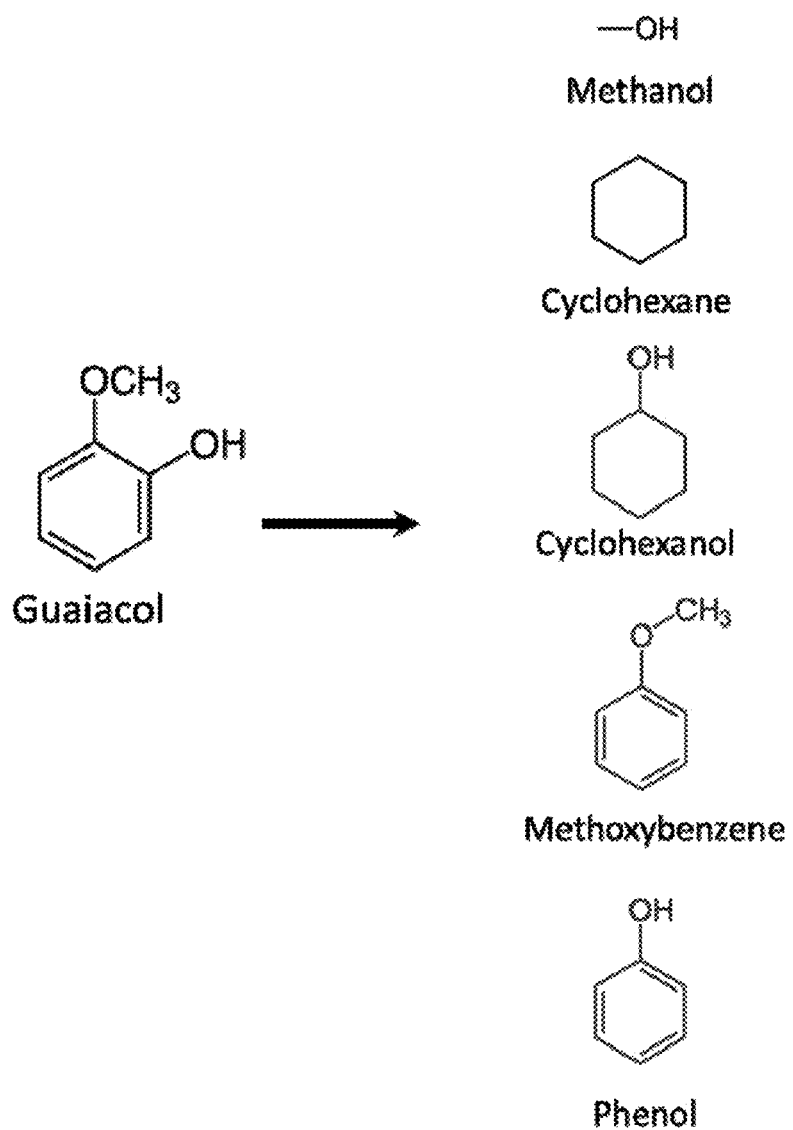
FIG. 5 is an exemplary product profile for the conversion of guaiacol using the catalysts and methods of the present invention. Specifically, the products shown were identified from the conversion of guaiacol using 2% Pd 2% Mo and 0.5% Sn on W—$ZrO_2$.

For both the guaiacol and ferulic acid feedstocks a ½ inch Inconel reactor was loaded with 12 grams of the trimetallic catalyst, which was then co-loaded with Calgon activated carbon resulting in a 12 inch total bed length. Guaiacol was fed to the reactor at a weight hour space velocity (WHSV) of 1.1 grams guaiacol per gram of catalyst per hour, with a water diluent at WHSV of 2.5 grams water per gram of catalyst per hour, resulting in an approximately 30 wt % guaiacol feedstock. The reactor was operated with a temperature profile of 180-260° C. at a pressure of 1050 psig. A non-exhaustive, exemplary product profile for the conversion of guaiacol over the HDO catalyst is shown in FIG. 5.

Figure 6:
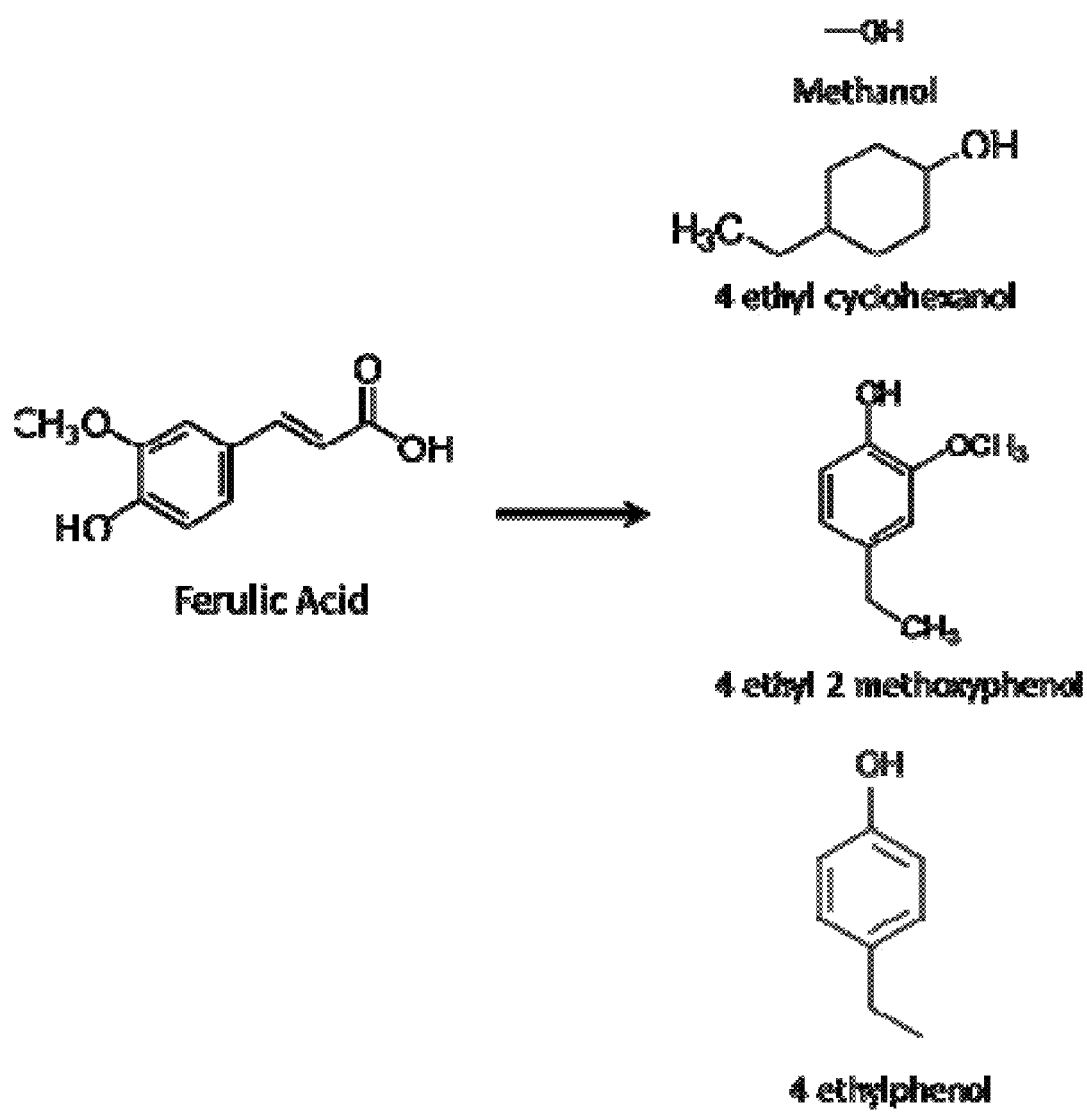
FIG. 6 is an exemplary product profile for the conversion of ferulic acid using the catalysts and methods of the present invention. Specifically, the products shown were identified from the conversion of ferulic acid using 2% Pd 2% Mo and 0.5% Sn on W—$ZrO_2$.

A 10 wt % feedstock solution of ferulic acid was fed to the reactor at a WHSV of 0.33 grams ferulic acid per gram of catalyst per hour. The reactor was operated with a temperature profile of 180-260° C. at a pressure of 1050 psig. A non-exhaustive, exemplary product profile for the conversion of ferulic acid over the HDO catalyst is shown in FIG. 6.

The product profiles show the reactivity of lignin species for hydrogenation, carbon-carbon bond cleavage, and carbon-oxygen bond cleavage. The resulting products demonstrate the feasibility of processing lignin based components over a trimetallic HDO catalyst to produce lower molecular weight oxygenated compounds that could be useful in the production of chemicals, liquid fuels, and other products/intermediates.

Example 35

A trimetallic catalyst containing 2 wt % palladium, 2 wt % molybdenum, and 0.5 wt % tin, supported on tungstated zirconia, was prepared using incipient wetness techniques. An aqueous solution of 2 molar ammonium nitrate (Sigma Aldrich) with a volume equal to the incipient wetness volume for the tungstated zirconia to be impregnated, 60 mL, and containing 2.2 g tin (IV) chloride pentahydrate (Riedel de Haen) was applied dropwise to 145 g tungstated zirconia (Norpro). The catalyst was dried at 120° C. under vacuum for 2 hours. The catalyst was then calcined with air at a gradient temperature reaching 400° C. over a period of 4 hours. Once the desired temperature was reached the catalyst was further soaked in air for an additional period of 6 hours. An aqueous solution of 2 molar ammonium nitrate (Sigma Aldrich) with a volume equal to the incipient wetness volume for the catalyst to be impregnated, 60 mL, and containing 5.4 g ammonium molybdate (VI) tetrahydrate (Sigma Aldrich) was applied dropwise to the calcined catalyst. The catalyst was dried at 120° C. under vacuum for 2 hours. An aqueous solution of 2 molar ammonium nitrate (Sigma Aldrich) with a volume equal to the incipient wetness volume for the catalyst to be impregnated, 50 mL, and containing 7.4 g palladium (II) nitrate hydrate was applied dropwise to the catalyst. The catalyst was dried at 120° C. under vacuum for 2 hours. The catalyst was then calcined with air at a gradient temperature reaching 400° C. over a period of 4 hours. Once the desired temperature was reached the catalyst was further soaked in air for an additional period of 6 hours.

Example 36

The incorporation of a high ionic strength impregnation solution in the catalyst preparation defined in Example 35 provides improvements to catalyst lifetime when compared to using DI water as the precursor diluent as defined in Example 24. Catalysts prepared with a high ionic strength impregnation solution and DI water were tested to determine their performance in converting a 60 wt % 43 DE food grade corn syrup to distillate range fuel products. Before feed was introduced, the catalysts were reduced using hydrogen at a space velocity of 700 hr$^{-1}$, a 3 hour temperature gradient to 320° C., followed by a 3 hour hydrogen soak. The HDO reactor had a temperature gradient from 220-300° C., 1050 psig and a WHSV of 0.5 grams sucrose per gram of corn syrup per hour. The hydrogen was provided at an H$_2$/carbon molar ratio of 2 and the aqueous recycle was set to a 4:1 recycle to fresh feed weight ratio.

Figure 7:
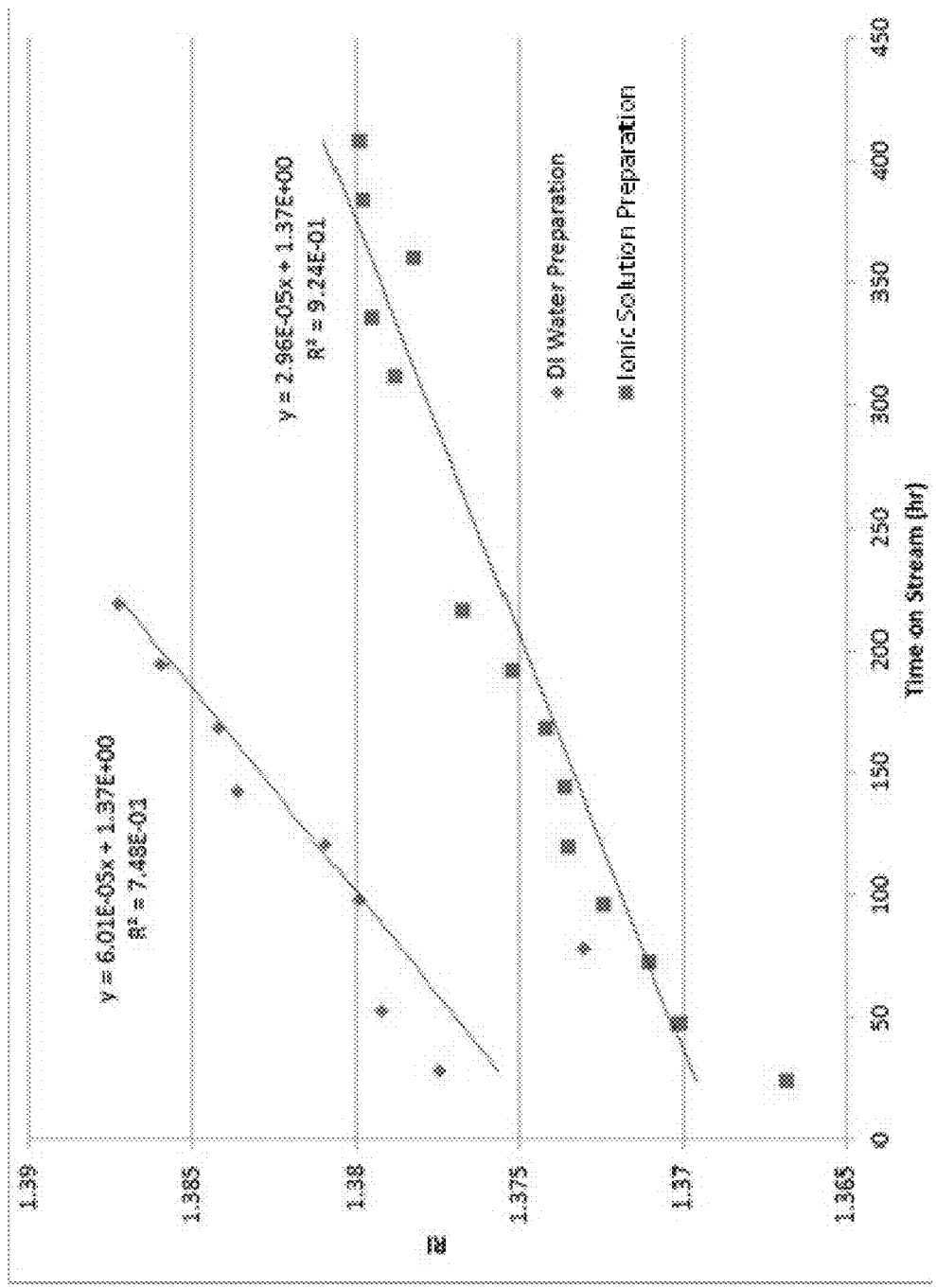
FIG. 7 is a chart illustrating the difference in relative catalyst deactivation rate using different solvents as catalyst precursor diluents.

The refractive index (RI) of the HDO product, which can be viewed as a representation of the amount of oxygen contained in the aqueous product liquid, is shown over time for these two HDO catalysts in FIG. 7. The incorporation of an ionic solvent as the diluent for the impregnation decreases the relative rate of catalyst deactivation by approximately half.

Example 37

For the hydrodeoxygenation of biomass derived feedstocks, operating pressure has significant impact on catalyst stability. The catalyst defined in Example 24 was tested to determine the impact of operating pressure on the conversion of a 60 wt % 43 DE food grade corn syrup to distillate range fuel products. Before feed was introduced, the catalyst was reduced using hydrogen at a space velocity of 700 hr$^{-1}$, a 3 hour temperature gradient to 320° C., followed by a 3 hour hydrogen soak. The HDO reactor had a temperature gradient from 220-300° C. or 170-300° C. at 1050 psig and 1800 psig respectively and a WHSV of 0.5 grams corn syrup per gram of catalyst per hour. The hydrogen was provided at an H$_2$/carbon molar ratio of 2 and the aqueous recycle was set to a 4:1 recycle to fresh feed weight ratio.

Figure 8:
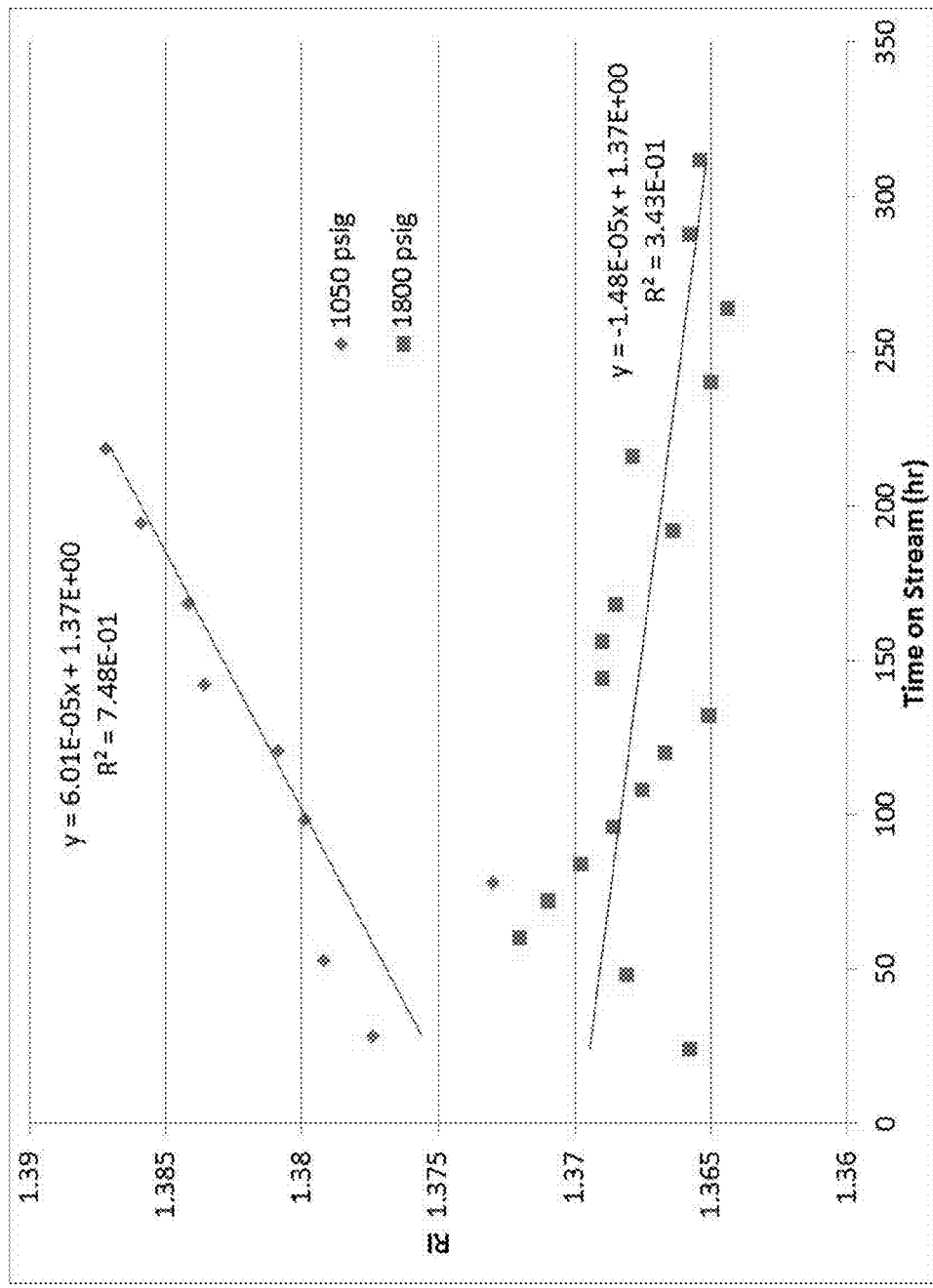
FIG. 8 is a chart illustrating the difference in relative catalyst deactivation rate using different reactor system pressures. Specifically, refractive index (RI) is plotted as a function of time on stream for two different pressures (1050 psig and 1800 psig).

The refractive index (RI) of the HDO product, which can be viewed as a representation of the amount of oxygen contained in the aqueous product liquid, is shown over time for these two pressures in FIG. 8. Increasing system pressure from 1050 psig to 1800 psig yields limited catalyst deactivation to potentially a slight improvement in catalytic activity over time.

The invention claimed is:

1. A heterogeneous catalyst, the heterogeneous catalyst comprising (i) a Group VIII metal, (ii) a member selected from the group consisting of molybdenum, tungsten, tin, and combinations thereof, and (iii) a metal oxide support,
wherein the heterogeneous catalyst is configured to produce a monooxygenated cyclic ether and/or a monooxygenated cyclic ketone when an aqueous oxygenated hydrocarbon feedstock solution, the aqueous feedstock solution comprising water and an oxygenated hydrocarbon selected from the group consisting of a starch, a sugar, a sugar alcohol, a polysaccharide, an oligosaccharide, a trisaccharide, a disaccharide, a monosaccharide, and combinations thereof, and hydrogen are contacted with the heterogeneous catalyst.

2. The heterogeneous catalyst of claim 1, wherein the Group VIII metal is palladium.

3. The heterogeneous catalyst of claim 1, wherein the heterogeneous catalyst comprises between 0.05 and 5.0 wt % palladium.

4. The heterogeneous catalyst of claim 1, wherein the heterogeneous catalyst comprises between 0.05 and 10.0 wt % molybdenum, between 0.0125 to 5.0 wt % tin, between 0.1 and 20.0 wt % tungsten, or combinations thereof.

5. The heterogeneous catalyst of claim 1, wherein the metal oxide support is an acidic support.

6. The heterogeneous catalyst of claim 1, wherein the metal oxide support is stable in the aqueous oxygenated hydrocarbon feedstock solution.

7. The heterogeneous catalyst of claim 1, wherein the metal oxide support is selected from the group consisting of alumina, zirconia, titania, vanadia, ceria, heteropolyacid, kieselguhr, zinc oxide, chromia, acidic alumina, silica-alumina, iron aluminate, theta alumina, niobia, and mixtures thereof.

8. The heterogeneous catalyst of claim 1, wherein the metal oxide support is modified with a modifier selected from the group consisting of tungsten, titania, sulfate, phosphate, and silica.

9. The heterogeneous catalyst of claim 1, wherein the metal oxide support is selected from the group consisting of tungstated zirconia, titania zirconia, sulfated zirconia, phosphated zirconia, and mixtures thereof.

10. A method for converting oxygenated hydrocarbons to cyclic ethers or cyclic ketones, the method comprising:
contacting an aqueous oxygenated hydrocarbon feedstock and hydrogen with the heterogeneous catalyst of claim 1 to produce a reaction product comprising a monooxygenated cyclic ether and/or a monooxygenated cyclic ketone in an amount greater than 1 wt % of the oxygenated hydrocarbon feedstock.

11. The method of claim 10, wherein the aqueous oxygenated hydrocarbon feedstock comprises water and one or more oxygenated hydrocarbons selected from the group consisting of a starch, a sugar, a sugar alcohol, a polysaccharide, an oligosaccharide, a trisaccharide, a disaccharide, a monosaccharide, and combinations thereof.

12. The method of claim 10, wherein the aqueous oxygenated hydrocarbon feedstock further comprises one or more oxygenated hydrocarbons selected from the group consisting of a polyhydric alcohol, a sugar degradation product, lignin, phenolics, methoxy-substituted phenolics, ash components, extractives, and combinations thereof.

13. The method of claim 10, wherein the reaction product comprises monooxygenated cyclic ethers and monooxygenated cyclic ketones.

14. The method of claim 10, wherein the reaction product further comprises one or more oxygenates selected from the group consisting of a polyol, a ketone, an aldehyde, a carboxylic acid, an alcohol, and combinations thereof.

15. The method of claim 10, wherein the oxygenated hydrocarbon feedstock is contacted with the heterogeneous catalyst at a reaction temperature between 100° C. and 300° C.

16. The method of claim 10, wherein the oxygenated hydrocarbon feedstock is contacted with the heterogeneous catalyst at the reaction pressure between 70 psig and 2000 psig.

17. The method of claim 10, wherein the oxygenated hydrocarbon feedstock is contacted with the heterogeneous catalyst at a weight hour space velocity of 0.01 to 10.0 grams of soluble oxygenated hydrocarbon per gram of heterogeneous catalyst per hour.

18. The method of claim 10, the method further comprising catalytically reacting a portion of the reaction product with a condensation catalyst to produce $C_{4+}$ compounds selected from the group consisting of a $C_{4+}$ alcohol, a $C_{4+}$ ketone, a $C_{4+}$ alkane, a $C_{4+}$ alkene, a $C_{5+}$ cycloalkane, a $C_{5+}$ cycloalkene, an aryl, and a fused aryl.

19. The method of claim 18, wherein the $C_{4+}$ compounds comprise an aryl selected from the group consisting of toluene, orthoxylene, metaxylene, paraxylene, ethylbenzene, and combinations thereof.

20. The method of claim 18, the method further comprising distilling the $C_{4+}$ compounds to provide a composition selected from the group consisting of an aromatic fraction, a gasoline fraction, a kerosene fraction, and a diesel fraction.

* * * * *